(12) United States Patent
Nishii et al.

(10) Patent No.: US 7,769,126 B2
(45) Date of Patent: Aug. 3, 2010

(54) COMPUTED TOMOGRAPHY SYSTEM

(75) Inventors: Yuichi Nishii, Tokyo (JP); Koji Takekoshi, Yokohama (JP); Tsukasa Sako, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 118 days.

(21) Appl. No.: 12/236,787

(22) Filed: Sep. 24, 2008

(65) Prior Publication Data

US 2009/0080595 A1    Mar. 26, 2009

(30) Foreign Application Priority Data

Sep. 25, 2007    (JP) .............................. 2007-248180

(51) Int. Cl.
*A61B 6/03* (2006.01)

(52) U.S. Cl. .......................................................... 378/4
(58) Field of Classification Search .................... 378/4, 378/19
See application file for complete search history.

(56) References Cited

U.S. PATENT DOCUMENTS

2005/0278408 A1    12/2005    Matsumoto

FOREIGN PATENT DOCUMENTS

JP    2005-334110    12/2005

*Primary Examiner*—Chih-Cheng G Kao
(74) *Attorney, Agent, or Firm*—Canon USA Inc IP Division

(57) ABSTRACT

A CT system performing reconstruction processing based on projection-image-data items obtained from a CT apparatus, wherein the CT system performs the reconstruction processing by, for example, distributing opposed projection-image-data items to a submachine as a single set.

3 Claims, 27 Drawing Sheets

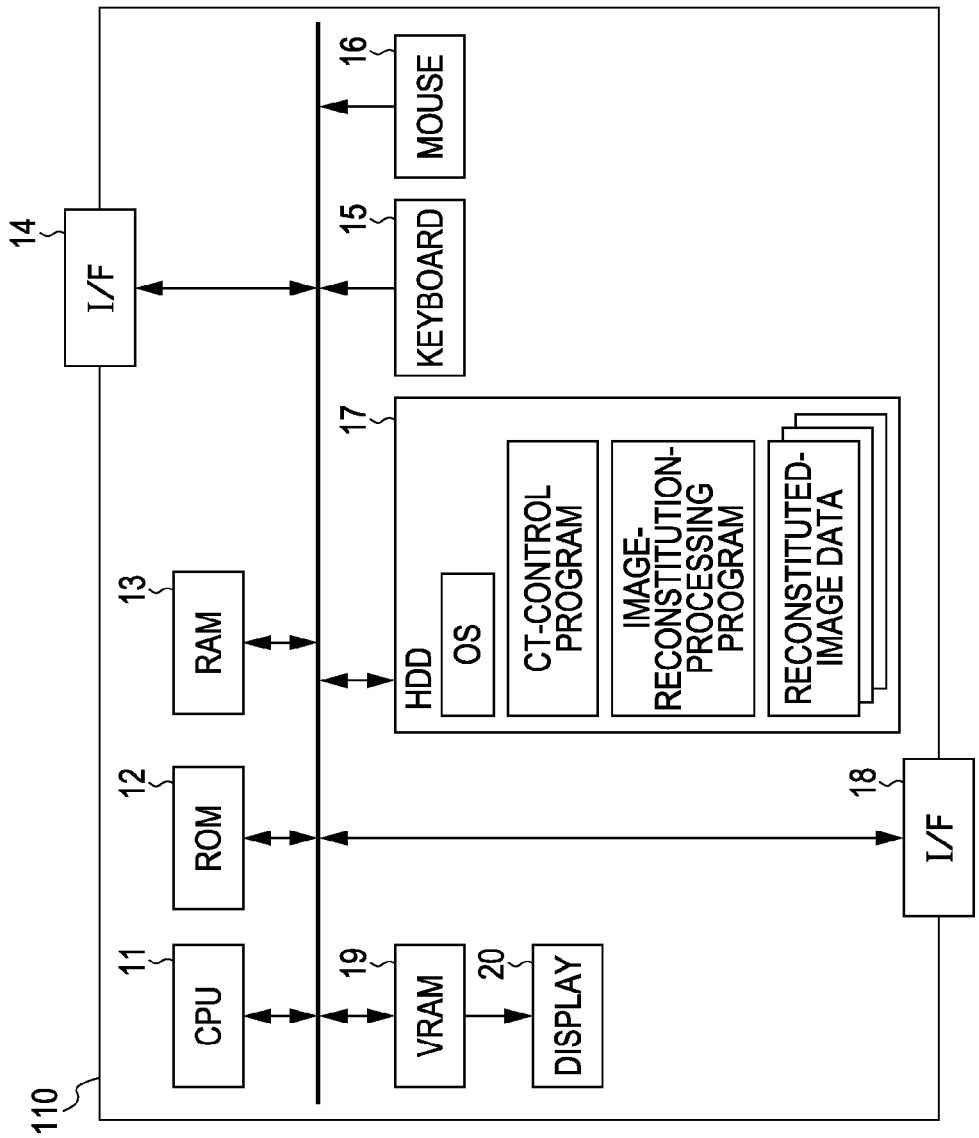

FIG. 20
PROJECTION IMAGE
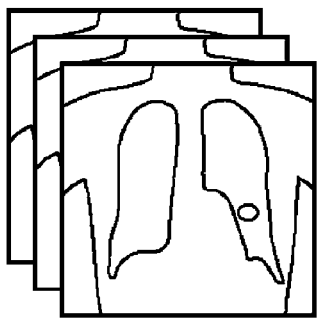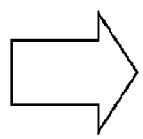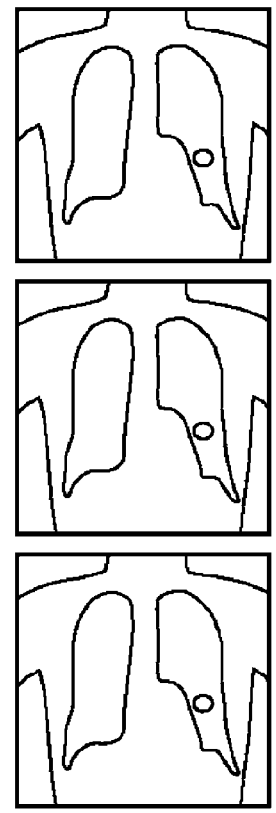
FIG. 21
PROJECTION IMAGE
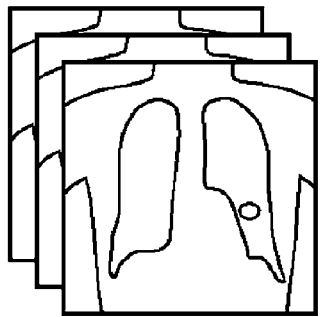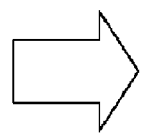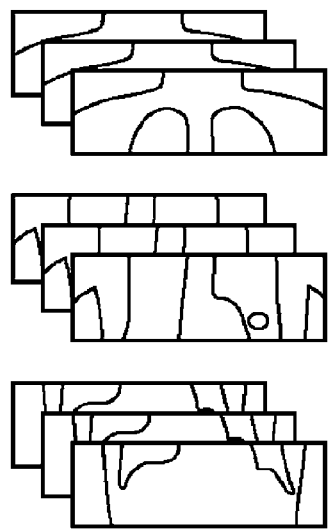

COMPUTED TOMOGRAPHY SYSTEM

BACKGROUND OF THE INVENTION

1. Field of the Invention

The present invention relates to a computed-tomography (CT) system configured to reconstruct the tomographic image of a subject based on projection-image data obtained by radiating radiation including an X-ray, etc. to the subject.

2. Description of the Related Art

CT apparatuses have been significantly advancing ever since they were invented. In recent years, the helical-scan method has been put to practical use, for example, so as to radiate an X-ray to a subject in a helical fashion by making an X-ray tube circle the periphery of the subject continually while moving the subject in the body-axis direction. Further, apparatuses that can perform tomographic imaging for obtaining slice images through a single rotation by using a two-dimension detector have been put to practical use.

CT apparatuses referred to as so-called third-generation CT apparatuses usually capture a tomographic image through the following procedures. First, an X-ray tube and a multichannel X-ray detector are provided so that they are opposed to each other and a subject is provided therebetween. An X-ray beam is radiated from the X-ray tube to the subject while making the X-ray tube and the X-ray detector rotate 360 degrees around the subject, and the X-ray that had passed through the subject is detected by the X-ray detector. At that time, the intensity of the X-ray radiated from the X-ray tube is constant (namely, the tube voltage and the tube current of the X-ray tube is constant). Here, the X-ray emitted from the focal point of the X-ray tube is collimated with a fan-shaped X-ray beam. Further, the spread width of the X-ray beam is determined based on the slice thickness, etc.

The above-described operations performed to radiate the X-ray from the X-ray tube to the subject by making the X-ray tube and the X-ray detector rotate around the subject and detect the X-ray transmitted through the subject by using the X-ray detector are referred to as "scanning". Further, a rotation angle at which the X-ray transmitted through the subject is detected (sampled) by using the X-ray detector during the above-described rotation is referred to as a "view angle". The tomographic image of the subject can be acquired by reconstructing the projection-image-data items corresponding to a plurality of views obtained through the above-described scanning.

Since the above-described X-ray CT apparatuses of late can capture many fine slice images at the same time, the X-ray-CT apparatuses have to reconstruct many slice images with high speed by using the projection-image-data items corresponding to captured views.

At present, Japanese Patent Laid-Open No. 2005-334110 discloses an example method of distributing the above-described reconstruction processing.

Thus, there have been requests for reconstructing many slice images due to the advance of the X-ray CT apparatuses. Therefore, pre-processing, convolution-calculation processing, and post-processing that have been considered as insignificant are put under heavy processing loads. Therefore, there has been the task of performing not only back-projection-calculation processing, but also the pre-processing, the convolution-calculation processing, and the post-processing with high speed.

SUMMARY OF THE INVENTION

Accordingly, the present invention has been achieved to perform the reconstruction processing with high speed.

Therefore, a computed-tomography system is provided according to an embodiment of the present invention, where the computed-tomography system includes a computed-tomography apparatus which performs scanning by radiating X-rays from at least two directions to a subject and collecting projection-image-data items, a host machine, connected to the computed-tomography apparatus, configured to instruct the computed-tomography apparatus to perform the scanning and to perform reconstruction processing based on the projection-image-data items transferred from the computed-tomography apparatus, and at least one submachine, connected to the host machine, configured to perform distribution processing for the reconstruction processing, wherein the host machine includes an input unit configured to input a distribution condition defining a condition for the distribution processing, a distribution unit configured to, based on the distribution condition, distribute projection-image-data items opposed to each other to the submachine as a set, and a reception unit configured to receive data transmitted from the submachine, the data being subjected to the distribution processing, and wherein the submachine includes an addition unit configured to perform addition, in a combination of the opposed projection-image-data items, for adding the pixel value of one of the projection-image data items to the pixel value of a coordinate position obtained by laterally reversing the other projection-image-data item, so as to be symmetric with respect to the rotation axis.

Further features of the present invention will become apparent from the following description of exemplary embodiments with reference to the attached drawings.

BRIEF DESCRIPTION OF THE DRAWINGS

FIG. 2A is a block diagram showing an example hardware configuration of a host machine according to the first embodiment.

FIG. 20 shows the case where projection-image data is distributed for each projection angle.

FIG. 21 shows the case where projection-image-data items divided along the body-axis direction are distributed.

DESCRIPTION OF THE EMBODIMENTS

Hereinafter, embodiments of the present invention will be described.

In the following embodiments, an X-ray is used, for example, as radiation.

First Embodiment

Figure 1A:
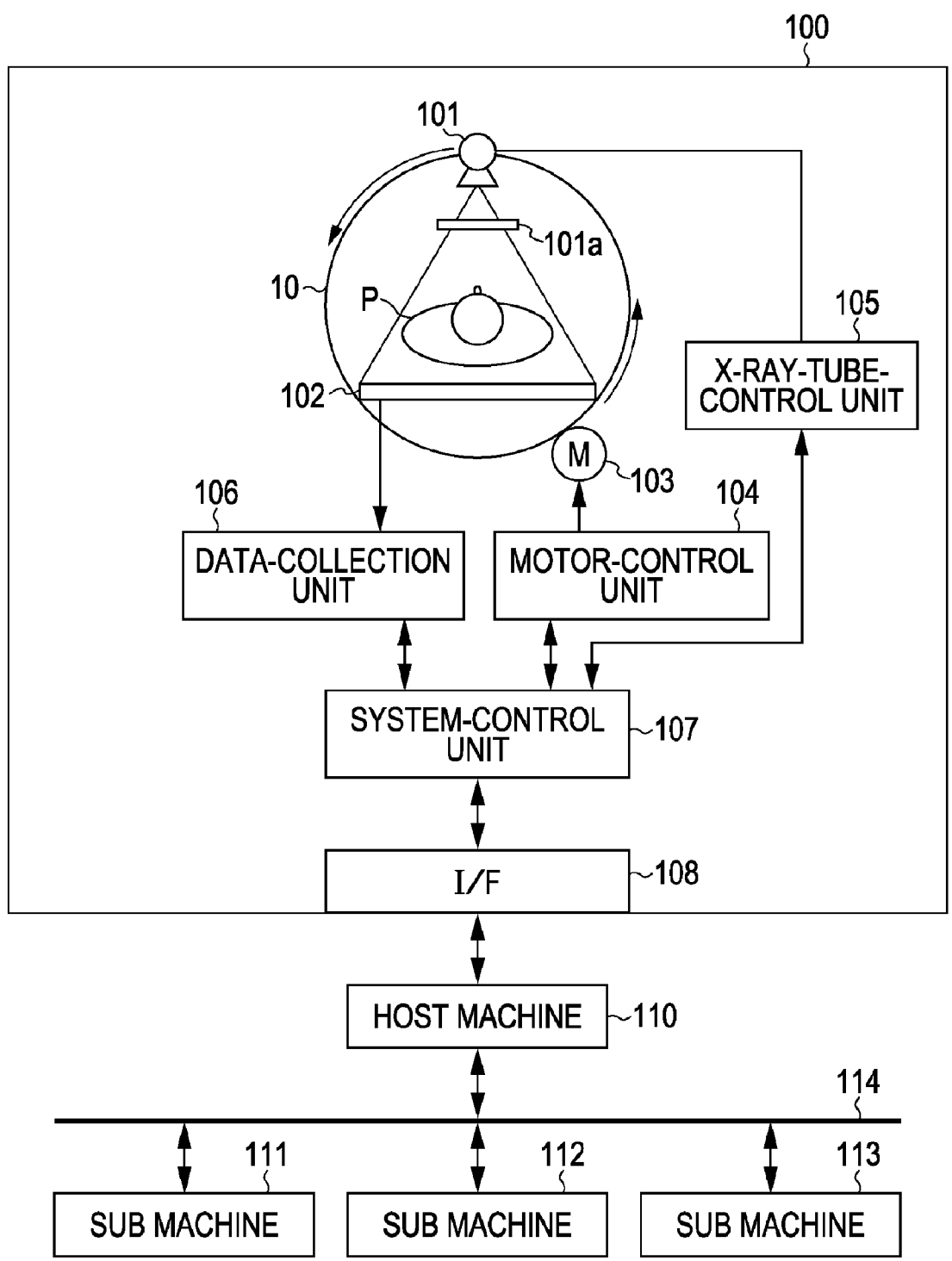
FIG. 1A is a block diagram showing an example configuration of an X-ray-CT system according to a first embodiment of the present invention.

FIG. 1A is a block diagram showing the configuration of an X-ray-CT system according to a first embodiment of the present invention.

As shown in FIG. 1A, the X-ray-CT system of the first embodiment includes a CT apparatus 100, a host machine 110, and submachines 111, 112, and 113.

In the CT apparatus 100, a gantry 10 includes a hollow section in which a subject P is inserted. An X-ray tube 101, which is an X-ray source, and a multichannel-X-ray detector 102, that is provided at a position opposed to the X-ray tube 101 via the subject P and that is configured to detect an X-ray transmitted through the subject P, are affixed to the gantry 10. Further, a collimator 101a is provided below the X-ray tube 101 to collimate an X-ray emitted from the focal point of the X-ray tube 101 with a fan-shaped X-ray beam (fan beam) spreading based on a determined slice thickness.

The gantry 10 is rotated by a motor 103 driven according to a drive signal transmitted from a motor-control unit 104. Due to the above-described rotation, the X-ray tube 101, the collimator 101a, and the X-ray detector 102 circle the periphery of the subject P as one body. While the above-described units are circling in the above-described manner, the subject P is radiated with an X-ray beam emitted from the X-ray tube 101 under the control of the X-ray-tube-control unit 105. The X-ray detector 102, which is two dimensional and flat shaped, detects an X-ray transmitted through the subject P (projection-image data). At that time, the intensity of the X-ray radiated from the X-ray tube 101 is constant (namely, the tube voltage and the tube current of the X-ray tube 101 are constant). The projection-image data detected by the X-ray detector 102 is accumulated in a data-collection unit 106.

The above-described operation including radiating X-rays from the X-ray tube 101 to the sample P from at least two directions while making the X-ray tube 101 and the X-ray detector 102 circle the periphery of the subject P and detecting X-rays transmitted through the subject P through the X-ray detector 102 is referred to as "scanning". Further, a rotation angle at which the transmitted X-rays are detected (sampled) through the X-ray detector 102 during the above-described rotation is referred to as a "view angle". Projection-image data detected by the X-ray detector 102 at a certain rotation angle centering on the body axis of the subject P in the above-described manner (projection-image data detected from a certain direction) is referred to as a "view". The projection-image data corresponding to at least two views obtained through the above-described scanning is transferred to the host machine 110 and the host machine 110 performs reconstruction processing so that a tomographic image of the subject P is generated.

Figure 1B:
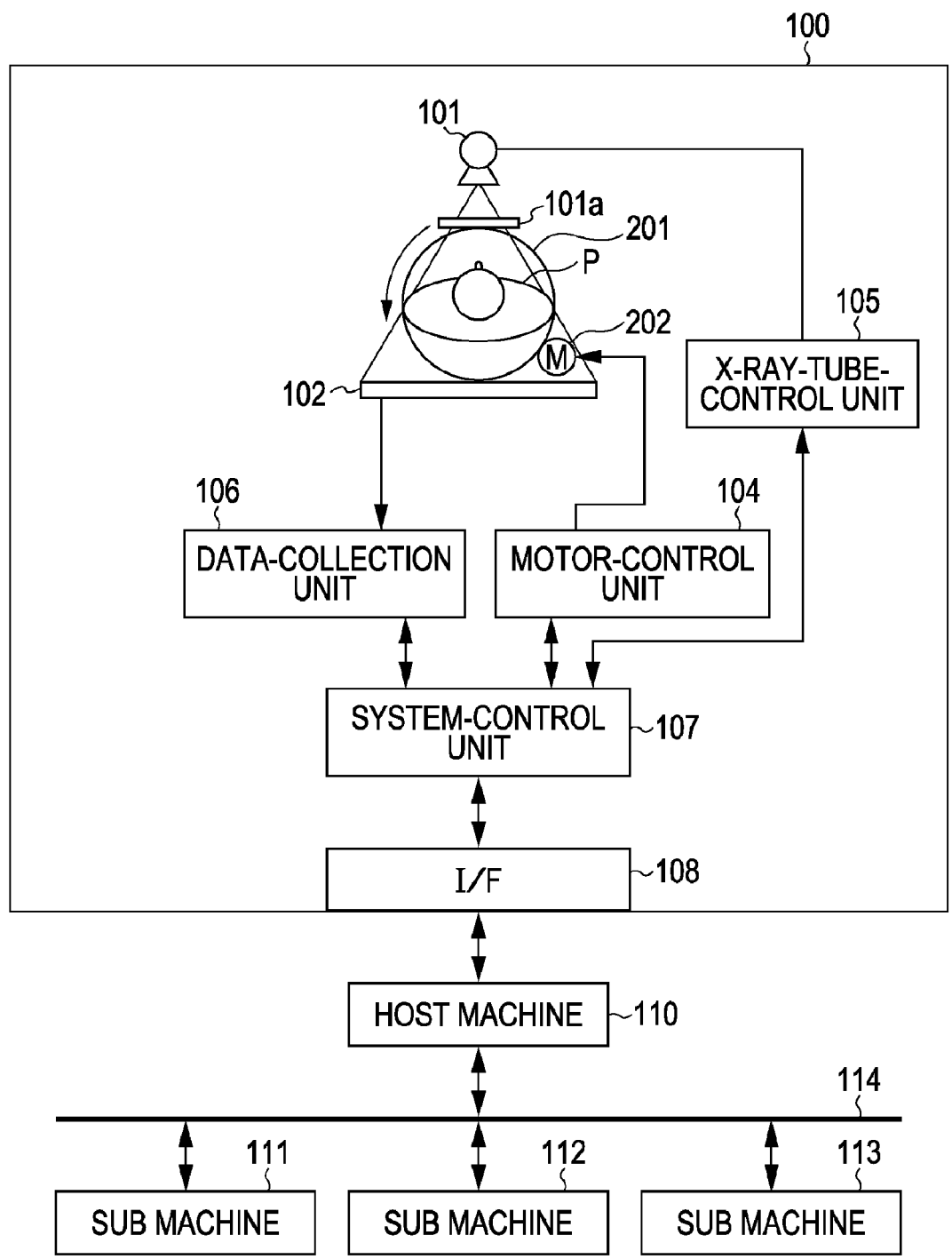
FIG. 1B is a block diagram showing another example configuration of the X-ray-CT system according to the first embodiment.

Another configuration may be used to perform the scanning without being limited to the above-described configuration. For example, as shown in FIG. B, a motor 202 (controlled by the motor-control unit 104) rotates a rotation table 201 on which the subject P is fixed without moving the X-ray tube 101, the collimator 101a, and the X-ray detector 102, as shown in FIG. 1B.

A system-control unit 107 has control over the motor-control unit 104, the X-ray-tube-control unit 105, and the data-collection unit 106 based on a command transmitted from the host machine 110 via an interface (I/F) 108. Further, the system-control unit 107 transfers the projection-image data collected by the data-collection unit 106 to the host machine 110 via the I/F 108.

The host machine 110 is a device provided to set and specify the scanning, reconstruct the transmitted projection-image data, and display the tomographic image, and is provided as a computer apparatus including a work station, etc. The host machine 110 is connected to at least one submachine via the network 114. In FIG. 1A, the three submachines 111 to 113 are connected to the host machine 110 via the network 114. However, the interconnection between the host machine 110 and the submachines 111 to 113 need not be via the network 114. Namely, the host machine 110 and the submachines 111 to 113 may be directly connected to one another by using cables, etc.

FIG. 2A shows an example hardware configuration of the host machine 110.

A CPU 11 is a central-processing device controlling the entire host machine 110. A read-only memory (ROM) 12 is provided to store stationary programs and/or data, and a random-access memory (RAM) 13 is a readable and writable memory provided to present a work area to the CPU 11 and temporarily store data, etc. An interface (I/F) 14 is connected to the above-described I/F 108. Each of a keyboard 15 and a mouse 16 is provided to make various types of settings. A hard-disk drive (HDD) 17 is a hard-disk device storing not only an operating system (OS), a CT-control program, and an image-reconstruction-processing program, but also data on reconstructed tomographic images (reconstructed-image data). An interface (I/F) 18 is connected to the network 114. A video RAM (VRAM) 19 is a memory configured to expand image data, and a display 20 is a display device configured to display the image data expanded by the VRAM 19.

Figure 2B:
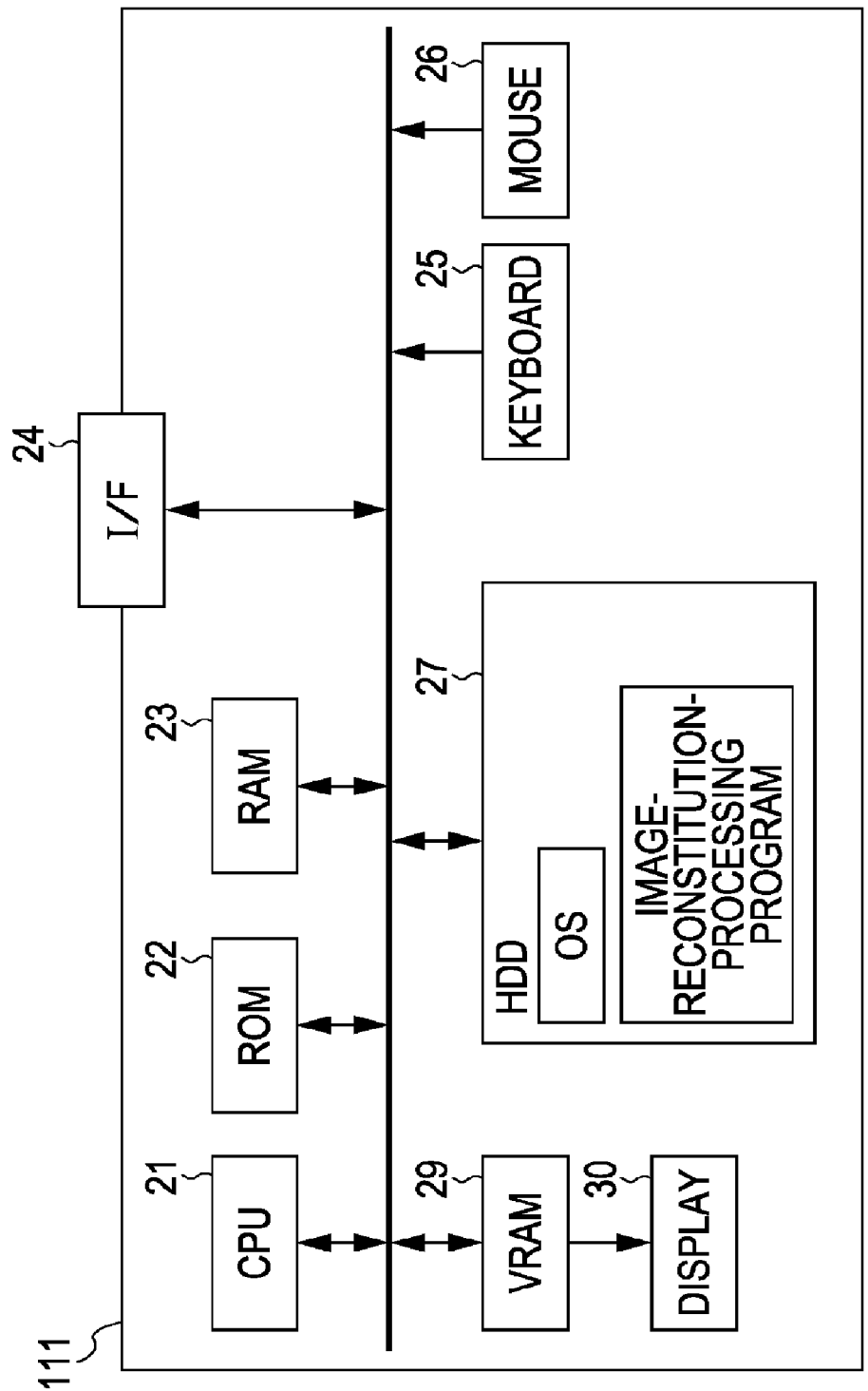
FIG. 2B is a block diagram showing an example hardware configuration of a submachine according to the first embodiment.

FIG. 2B shows an example hardware configuration of the submachine 111. Each of the submachines 112 and 113 has the same configuration as that of the submachine 111.

The CPU 21 is a central-processing device controlling the entire submachine 111. A ROM 22 is a read-only memory provided to store stationary programs and/or data, and a RAM 23 is a readable and writable memory provided to present the work area of the CPU 21 and temporarily store data, etc. An I/F 24 is connected to the network 114. Each of a keyboard 25 and a mouse 26 is provided to make various types of settings. An HDD 27 is a hard-disk device storing an operating system (OS) and/or an image-reconstruction-processing program. A VRAM 29 is a memory configured to expand image data, and a display 30 is a display device configured to display the image data expanded by the VRAM 29.

Figure 3:
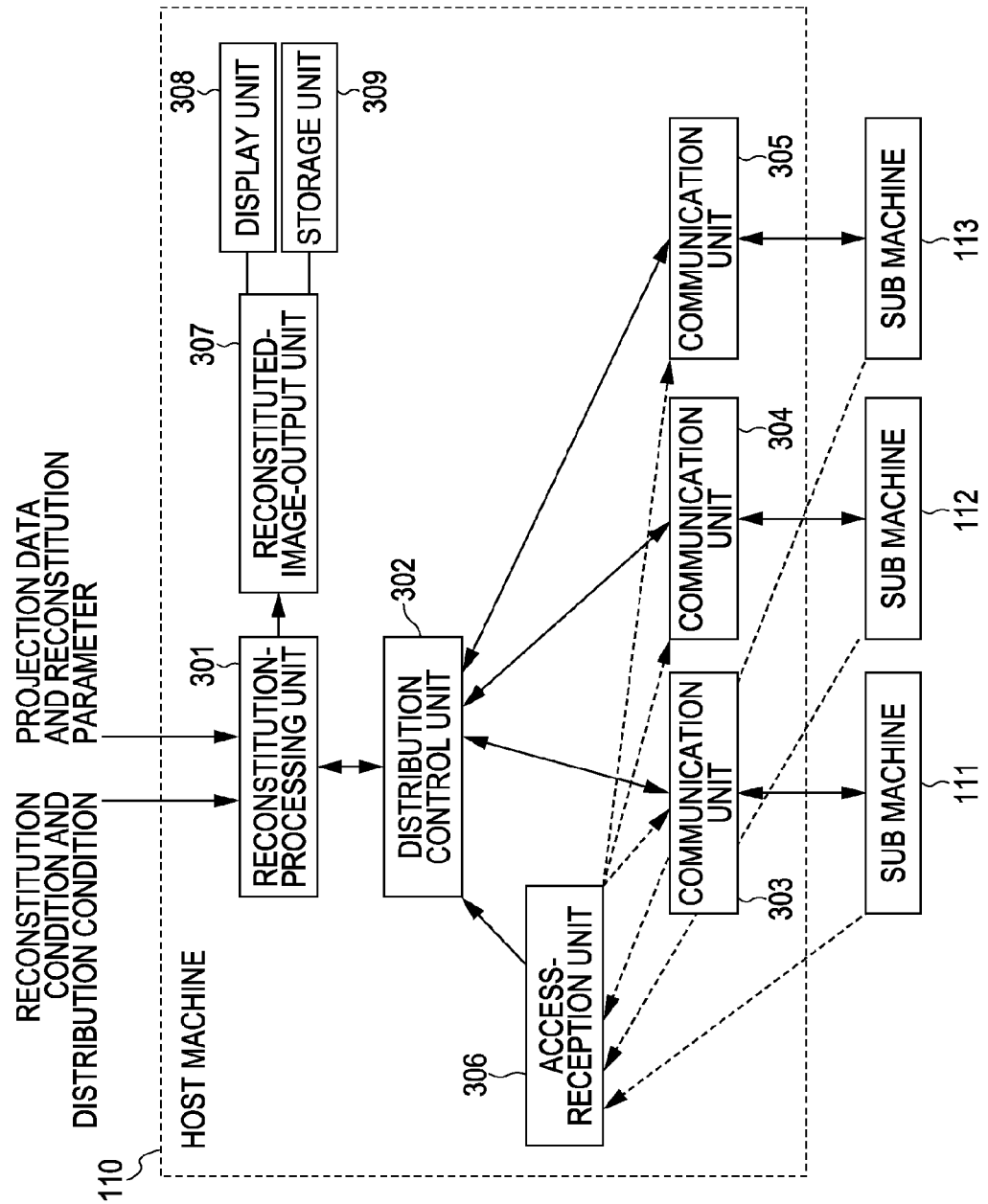
FIG. 3 is a functional block diagram relating to image-reconstruction processing performed by the host machine according to the first embodiment.

FIG. 3 is a block diagram showing functions relating to the image-reconstruction processing performed by the host machine 110. A program achieving the above-described functions is included in the CT-control program and/or the image-reconstruction-processing program operating with the CT-control program, where the CT-control program and the image-reconstruction-processing program are installed in the HDD 17, and is executed by the CPU 11.

A reconstruction-processing unit 301 inputs data on a reconstruction condition and a distribution condition, the data being input by a user via the keyboard 15 and/or the mouse 16. The distribution condition defines a condition for performing distribution processing and includes information about distribution items, where the distribution-item information indicates for which items, namely, pre-processing, convolution-calculation processing, back-projection processing, and post-processing the distribution processing should be performed.

Further, the reconstruction-processing unit 301 receives data on reconstruction parameters and projection-image data that are collected by the data-collection unit 106 and that are transferred via the system-control unit 107 and the I/F 108.

After that, the reconstruction-processing unit 301 transfers the above-described distribution condition, and part of the received reconstruction-parameter data and projection-image data, the part relating to the distribution processing, to a distribution-control unit 302 based on the input distribution condition. The other projection-image data is processed by the reconstruction-processing unit 301.

Figure 4:
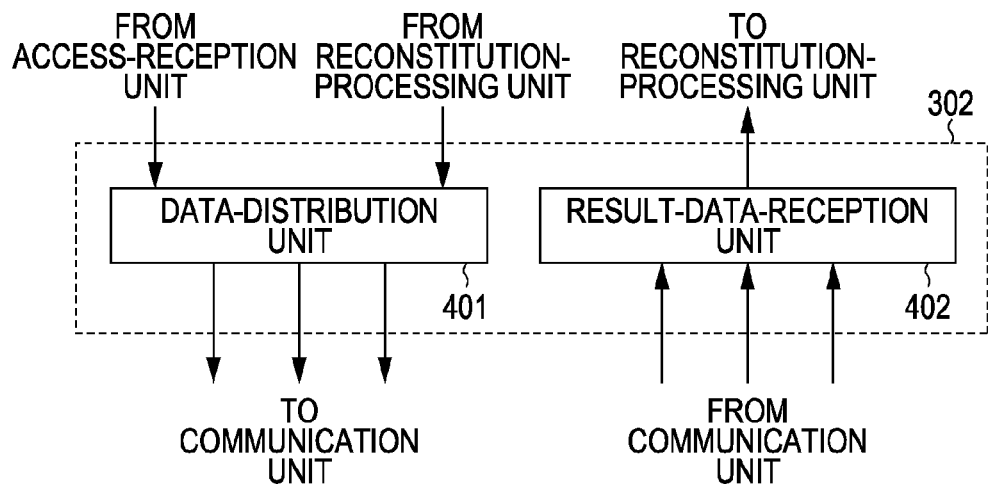
FIG. 4 shows the specific configuration of a distribution-control unit according to the first embodiment.

The distribution-control unit 302 includes a data-distribution unit 401 and a result-data-reception unit 402, as shown in FIG. 4. The data-distribution unit 401 samples a projection angle for the reconstruction-parameter data and the projection-image data that are transmitted from the reconstruction-processing unit 301 based on the distribution condition, and transmits the reconstruction-parameter data and the projection-image data to the submachines 111, 112, and 113 via communication units 303, 304, and 305. The result-data-reception unit 402 receives result data transmitted from each of the submachines 111 to 113 via the communication units 303 to 305, and transfers the result data to the reconstruction-processing unit 301.

An access-reception unit 306 controls the connection of each of the submachines 111 to 113, and generates the communication unit corresponding to a submachine for which connection confirmation was done. Further, the access-reception unit 306 informs the distribution-control unit 302 of the number of connected submachines.

The communication units 303 to 305 transmit the distribution-condition data, the reconstruction-parameter data, and the projection-image data that are transmitted from the distribution-control unit 302 to the submachines 111 to 113, respectively. Further, the communication units 303 to 305 receive data on a reconstructed image, the data being transmitted from the submachines 111 to 113, respectively.

A reconstructed-image-output unit 307 transmits reconstructed-image data compiled by the reconstruction-processing unit 301 to a display unit 308 (achieved by the VRAM 19 and the display 20) and/or a storage unit 309 (achieved by the HDD 17).

Figure 5:
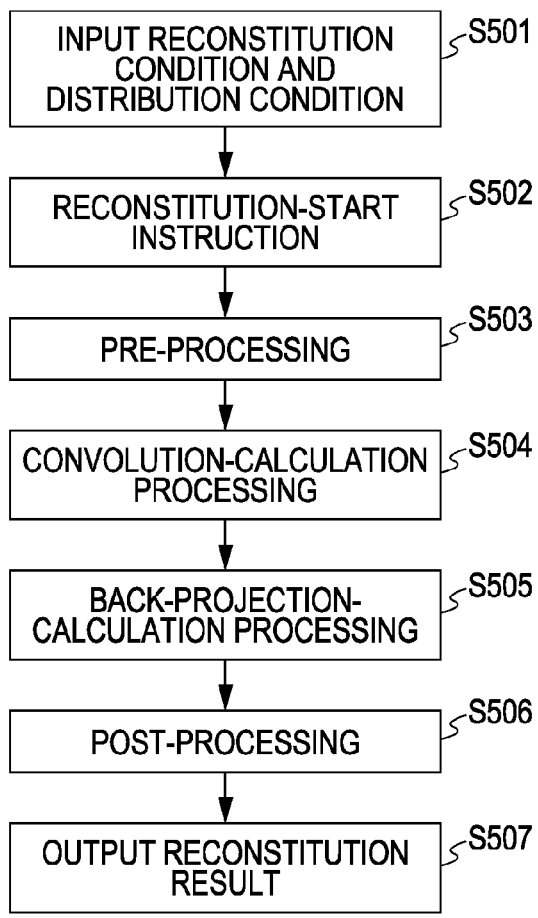
FIG. 5 is a flowchart showing the general outline of the image-reconstruction processing according to the first embodiment.

FIG. 5 is a flowchart indicating the general outline of ordinary image-reconstruction processing executed by, for example, the reconstruction-processing unit 301 of the host machine 110. A program capable of executing processing procedures illustrated in the flowchart is included in the image-reconstruction-processing program installed in each of the host machine 110, and the submachines 111, 112, and 113. Therefore, the above-described program can be executed by each of the submachines 111 to 113.

First, in step S501, the reconstruction-processing unit 301 inputs data on a reconstruction condition and a distribution condition that are set by the user operating the keyboard 15 and/or the mouse 16. Then, in step S502, when a reconstruction-start instruction is issued by the user operating the keyboard 15 and/or the mouse 16, the scanning is started. During the scanning, the reconstruction-parameter data and the projection-image data that are collected by the data-collection unit 106 and that are transferred via the system-control unit 107 and the I/F 108 are received and reconstruction is started.

First, pre-processing is performed at step S503. The pre-processing includes correction and/or coordinate transformation required to perform the reconstruction. The correction required to perform the reconstruction includes, for example, dark (dark current) correction, water correction performed to correct the pixel value of a projection image so that the pixel value becomes a value determined with reference to the X-ray-absorption coefficient of water, beam-hardening correction, etc. Further, the coordinate transformation includes fan/parallel conversion performed to convert fan-beam data into parallel-beam data, a direct method performed to calculate a weight coefficient, etc.

Next, convolution-calculation processing is performed at step S504 to correct a blur occurring in the projection-image data by subjecting the projection-image data to convolution integration by using a known function referred to as a filter function (reconstruction function). Further, back-projection-calculation processing is performed at step S505. The back-projection-calculation processing denotes radiating X-rays to a subject from various angles and obtaining the pixel value of real-space coordinates based on an observed intensity distribution (performing the reconstruction).

Next, in step S506, reconstructed-image data is generated by performing post-processing including digital-imaging-and-communication-in-medicine (DICOM) conversion processing, joint-photographic-experts-group (JPEG) compression processing, etc. In step S507, The reconstructed-image-output unit 307 transmits the reconstructed-image data to the display unit 308 so that display processing is performed, and transmits and stores the reconstructed-image data in the storage unit 309.

Figure 6:
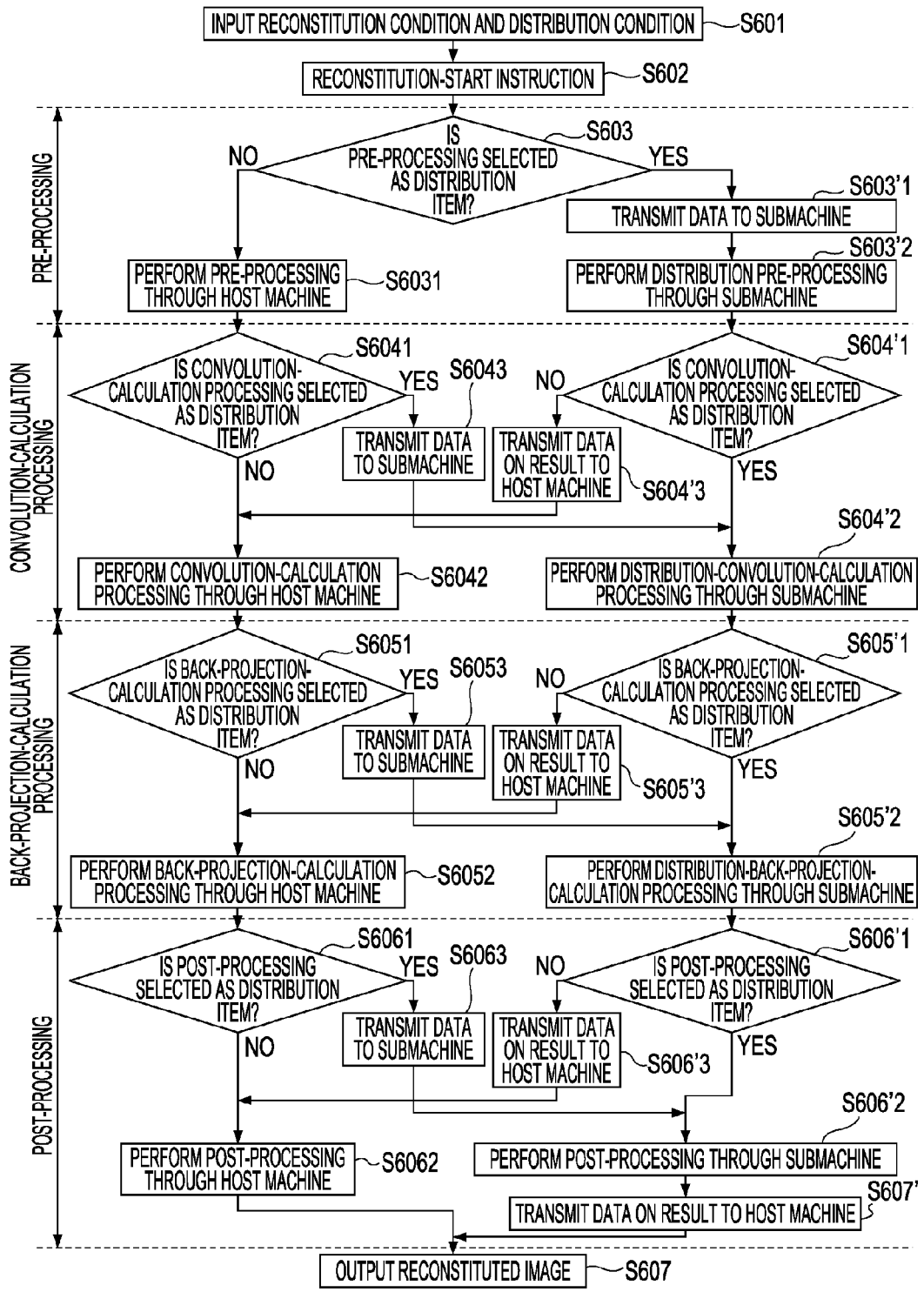
FIG. 6 is a flowchart showing the details on image-reconstruction processing including distribution processing according to the first embodiment.

FIG. 6 is a flowchart showing details on the image-reconstruction processing including the distribution processing according to the present embodiment.

First, in step S601, the reconstruction-processing unit 301 of the host machine 110 inputs data on a reconstruction condition and a distribution condition that are set by the user operating the keyboard 15 and/or the mouse 16. Then, in step S602, when a reconstruction-start instruction is issued by the user operating the keyboard 15 and/or the mouse 16, the scanning is started. During the scanning, the reconstruction-parameter data and the projection-image data that are collected by the data-collection unit 106 and that are transferred via the system-control unit 107 and the I/F 108 are received and the reconstruction is started.

In step S602, the reconstruction-processing unit 301 determines whether the pre-processing is selected as a distribution item based on the input distribution-condition data. If the pre-processing is selected as the distribution item, the data-distribution unit 401 of the distribution-control unit 302 distributes projection-image-data items based on the distribution-condition data and transmits the projection-image-data items to the corresponding submachines in step S603'1. Upon receiving the projection-image-data item, the submachine performs the pre-processing in step S603'2. On the other hand, when the pre-processing is not selected as the distribution item, the reconstruction-processing unit 301 of the host machine 110 performs the pre-processing in step S6031.

Next, the processing moves to the convolution-calculation processing.

If the reconstruction-processing unit 301 of the host machine 110 performs the pre-processing in step S6031, in step S6041, a determination is made whether the convolution-calculation processing is selected as the distribution item based on the distribution condition. When the convolution-calculation processing is selected as the distribution item, the data-distribution unit 401 of the distribution-control unit 302 distributes the projection-image-data items based on the distribution condition and transmits the projection-image-data items to the corresponding submachines in step S6043. Upon receiving the projection-image-data item, the submachine performs the convolution-calculation processing in step S604'2. On the other hand, when the convolution-calculation processing is not selected as the distribution item, the reconstruction-processing unit 301 of the host machine 110 performs the convolution-calculation processing in step S6042.

When the submachine performs the pre-processing in step S603'2, in step S604'1, a determination is made whether the convolution-calculation processing is selected as the distribution item based on the distribution condition. When the convolution-calculation processing is selected as the distribution item, the submachine performs the convolution-calculation processing in step S604'2 for the projection-image data subjected to the pre-processing in step S603'2. On the other hand, when the convolution-calculation processing is not selected as the distribution item, the submachine transmits the projection-image data subjected to the pre-processing in step S603'2 to the host machine 110, as result data in step S604'3. On the host machine 110-side, the result-data-reception unit 402 of the distribution-control unit 302 compiles and returns the transmitted result data to the reconstruction-processing unit 301. Then, the reconstruction-processing unit 301 performs the convolution-calculation processing in step S6042.

Next, the back-projection-calculation processing and the post-processing are performed in sequence, and each processing has the same flow as that of the above-described convolution-calculation processing.

If the reconstruction-processing unit 301 of the host machine 110 performs the convolution-calculation processing at step S6042, in step S6051, a determination is made whether the back-projection-calculation processing is selected as the distribution item based on the distribution condition. When the back-projection-calculation processing is selected as the distribution item, the data-distribution unit 401 of the distribution-control unit 302 distributes data items subjected to the convolution-calculation processing based on the distribution condition and transmits the data items to the corresponding submachines in step S6053. Upon receiving the data item, the submachine performs the back-projection-calculation processing in step S605'2. Data on the results of the back-projection-calculation processing performed by the submachines is temporarily compiled in the host machine 110 because the result data has no meaning per se. Then, the compiled pixel values of the coordinates of the real spaces are respectively added to the result data in the host machine 110 so that the definitive result of the back-projection calculation is obtained. On the other hand, when the back-projection-calculation processing is not selected as the distribution item, the reconstruction-processing unit 301 of the host machine 110 performs the back-projection-calculation processing in step S6052.

When the submachine performs the convolution-calculation processing in step S604'2, in step S605'1, a determination is made whether the back-projection-calculation processing is selected as the distribution item based on the distribution condition. When the back-projection-calculation processing is selected as the distribution item, the above-described submachine performs the back-projection-calculation processing in step S605'2, for the data subjected to the convolution-calculation processing in step S604'2. On the other hand, when the back-projection-calculation processing is not selected as the distribution item, the data subjected to the convolution-calculation processing in step S604'2 is transmitted to the host machine 110 as result data in step S605'3. On the host machine 110-side, the result-data-reception unit 402 of the distribution-control unit 302 compiles and returns the transmitted result data to the reconstruction-processing unit 301. Then, the reconstruction-processing unit 301 performs the back-projection-calculation processing in step S6052.

The post-processing is performed as below.

When the reconstruction-processing unit 301 of the host machine 110 performs the back-projection-calculation processing in step S6052, in step S6061, a determination is made whether the post-processing is selected as the distribution item based on the distribution condition in step S6061. When the post-processing is selected as the distribution item, the data-distribution unit 401 of the distribution-control unit 302 distributes reconstructed-image-data items subjected to the back-projection-calculation processing and transmits the reconstructed-image-data items to the corresponding submachines based on the distribution condition in step S6063. Upon receiving the reconstructed-image-data item, the submachine performs the post-processing in step S606'2. On the other hand, when the post-processing is not selected as the distribution item, the reconstruction-processing unit 301 of the host machine 110 performs the post-processing in step S6062.

When the submachine performs the back-projection-calculation processing in step S605'2, in step S606'1, a determination is made whether the post-processing is selected as the distribution item based on the distribution condition. When the post-processing is selected as the distribution item, the above-described submachine performs the post-processing in step S606'2. On the other hand, when the post-processing is not selected as the distribution item, the reconstructed-image data subjected to the back-projection-calculation processing in step S605'2 is transmitted to the host machine 110 as result data in step S606'3. On the host machine 110-side, the result-data-reception unit 402 of the distribution-control unit 302 compiles and returns the transmitted result data to the reconstruction-processing unit 301. Then, the reconstruction-processing unit 301 performs the post-processing in step S6062.

When the post-processing is performed by the submachine in step S606'2, data on the result of the above-described post-processing is transferred to the host machine 110 in step S607'. In that case, on the host machine-110 side, the result-data-reception unit 402 of the distribution-control unit 302 compiles and returns the transmitted result data to the reconstruction-processing unit 301.

Then, the reconstruction-processing unit 301 transmits the reconstructed-image data to the display unit 308 so that the display processing is performed, and transmits and stores the reconstructed-image data in the storage unit 309 in step S607.

Figure 7:
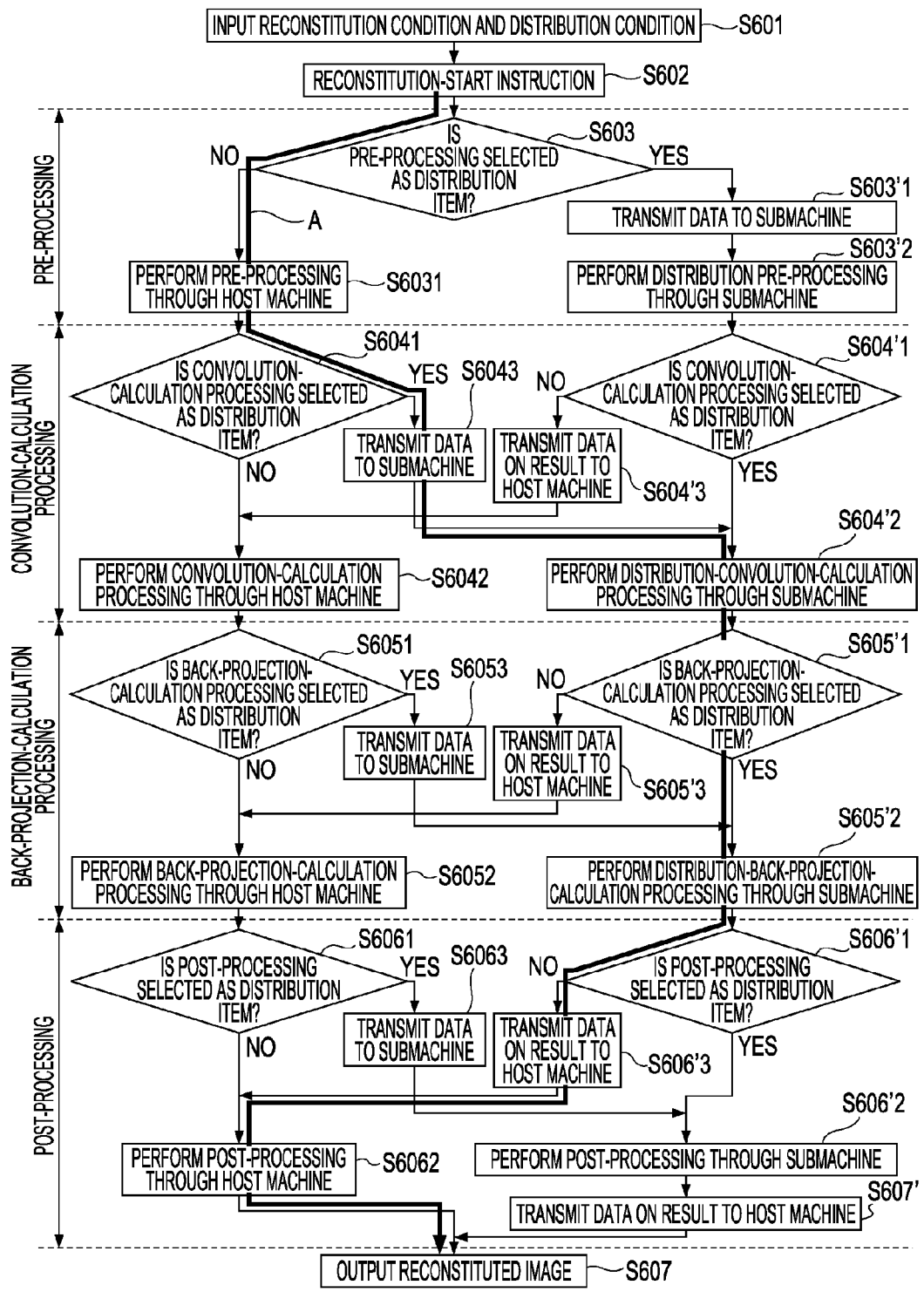
FIG. 7 illustrates an example based on the flowchart of FIG. 6.
Figure 8:
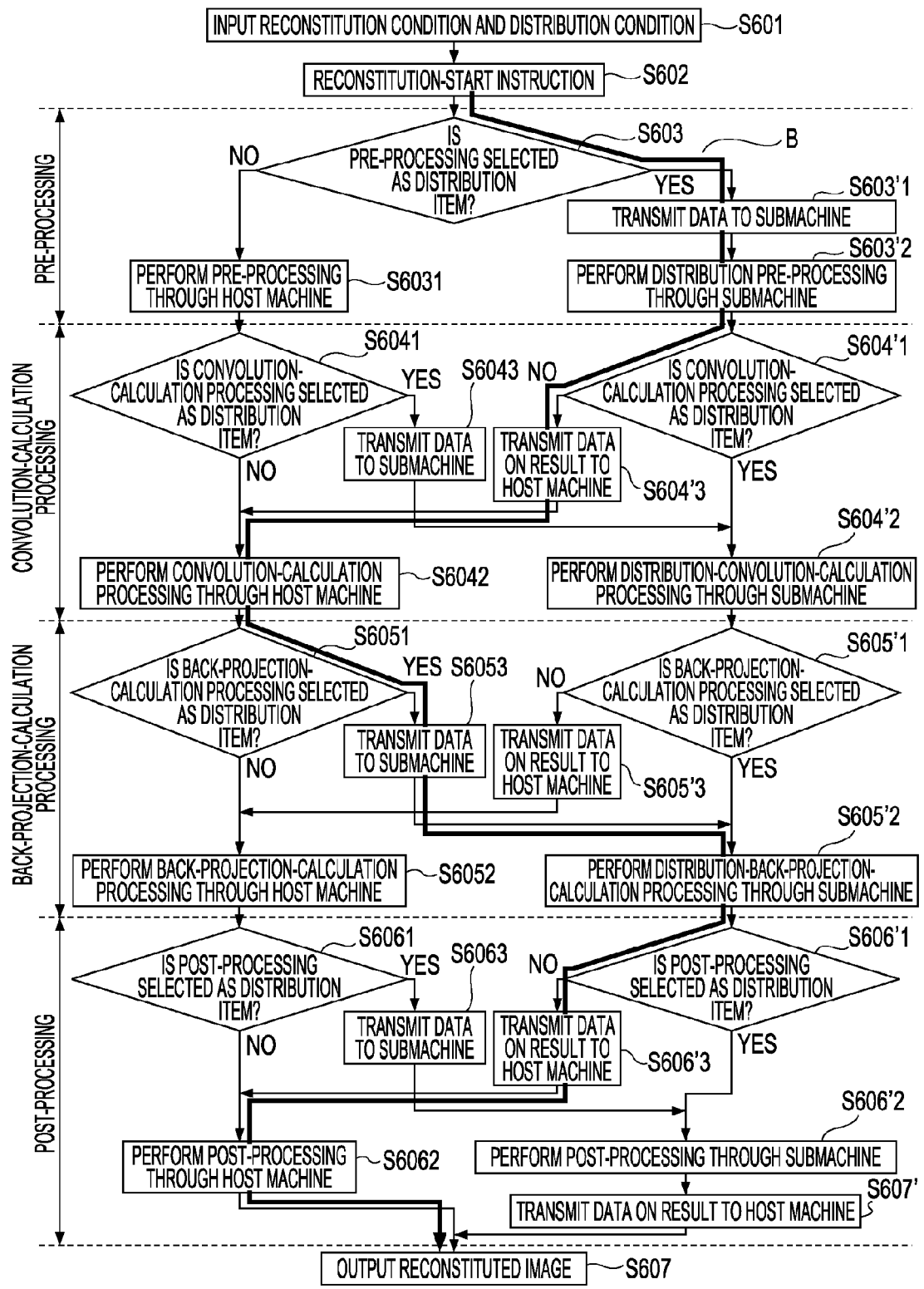
FIG. 8 illustrates an example based on the flowchart of FIG. 6.

FIG. 7 shows the flow of one example when the processing procedures shown in FIG. 6 are performed. FIG. 8 shows another example when the processing procedures shown in the flowchart of the FIG. 6 are performed.

In the example depicted in FIG. 7, both the convolution-calculation processing and the back-projection-calculation processing are selected as the distribution item, and the processing procedures are performed with the flow indicated by thick line A. In the second example depicted in FIG. 8, both the pre-processing and the back-projection-calculation processing are selected as the distribution item, and the processing procedures are performed with the flow indicated by thick line B.

When successive processing procedures, such as those shown in the first example (that is, the convolution-calculation processing and the back-projection-calculation processing) are selected as the distribution items, the frequency of data exchanges performed between the host machine and the submachines becomes smaller than that achieved in the case where other processing procedures are selected as the distribution items.

Next, a method of distributing the projection-image-data items to the submachines will be described at steps S603'1, S6043, and S6053 shown in FIG. 6.

For example, if it is determined that full scanning (360-degree projection), 1020 views, and three submachines are used, the following four methods may be considered as methods for sampling a projection angle.

Figure 9:
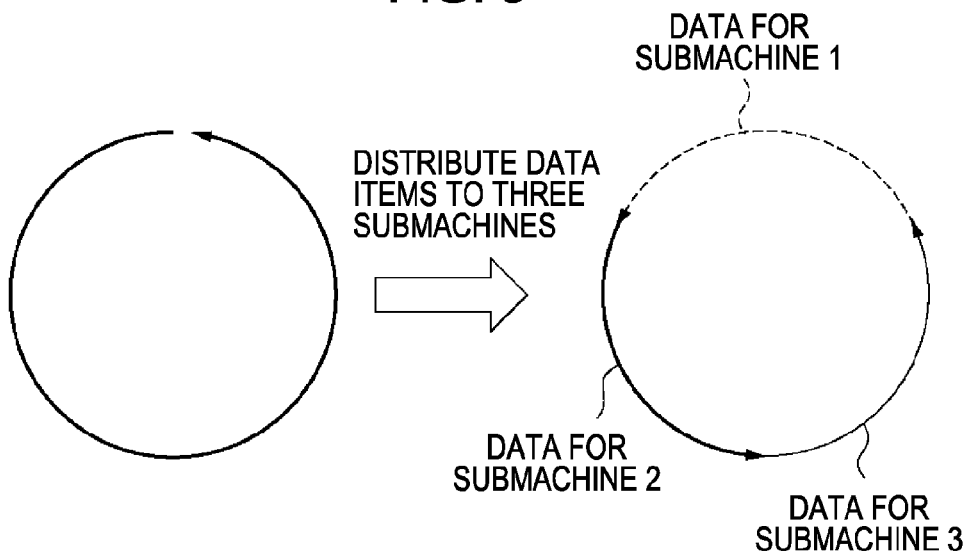
FIG. 9 shows an example method of distributing projection-image-data items at continuous angles.

(1) The views are distributed to the three submachines at continuous angles, as shown in FIG. 9. For example, the 340 views corresponding to a 120-degree angle are assigned to each of the submachines.

Figure 10:
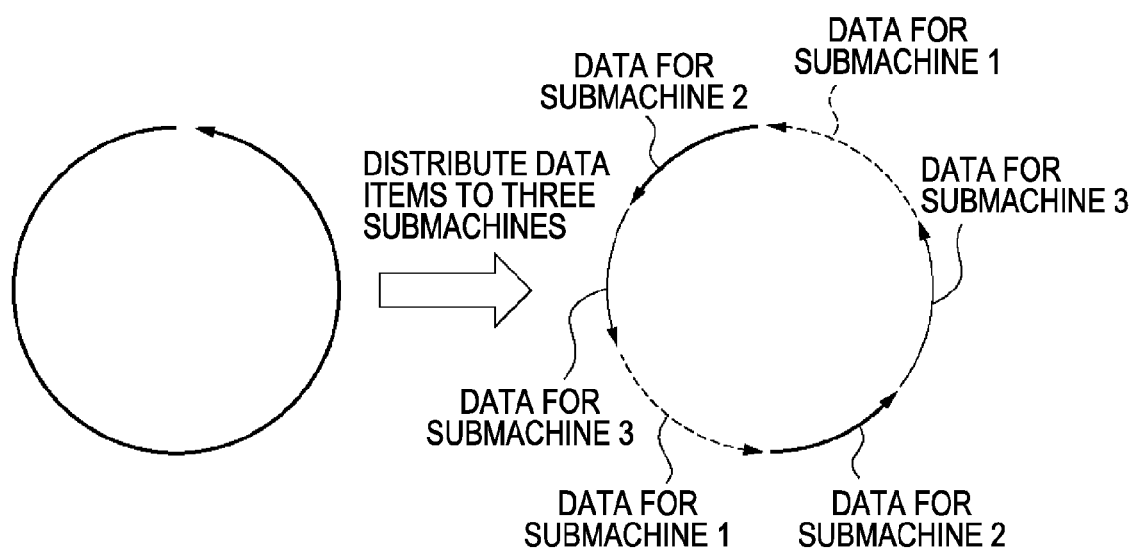
FIG. 10 shows an example method of distributing projection-image-data items by determining data items opposed to each other to be a set.

(2) Data items opposed to one another are distributed, as a set, as shown in FIG. 10. For example, the 170 views corresponding to a 120-degree angle and the other 170 views corresponding to a 120-degree angle opposed to the above-described 120-degree angle are assigned to each of the submachines.

Figure 13:
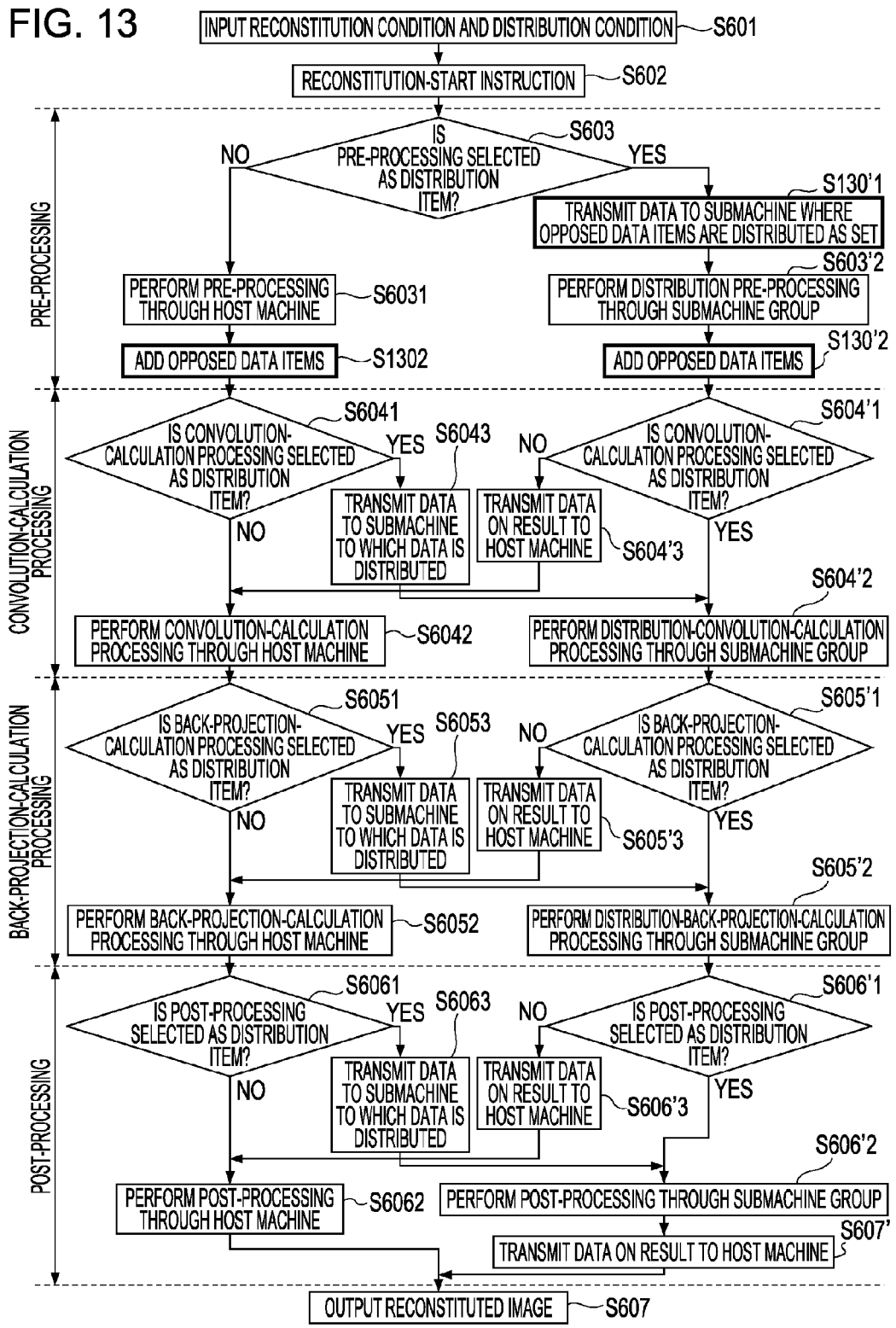
FIG. 13 is a flowchart showing details on image-reconstruction processing including distribution processing performed to distribute projection-image-data items by determining data items opposed to each other to be a set.

When using the method shown in FIG. 10, the convolution-calculation processing and the back-projection-calculation processing can be executed by performing half the calculations required for other methods. FIG. 13 is a flowchart showing details on image-reconstruction-processing procedures including distribution processing, the image-reconstruction-processing procedures being performed when the above-described method shown in FIG. 10 is used. At steps S1302 and S130'2, in each combination of opposing groups of projection-image-data items, the submachine and/or a main machine adds the pixel value of one of the above-described groups to that of a coordinate position of the other group laterally reversed in advance to be symmetric with respect to the rotation axis after the pre-processing is performed. Since the number of the views is halved by the above-described addition, the convolution-calculation processing and the back-projection-calculation processing can be executed by performing half the calculations required in the past.

When distribution processing is performed for the pre-processing, data items opposed to each other are distributed to the submachine as a set without fail in step S130'1.

Figure 11:
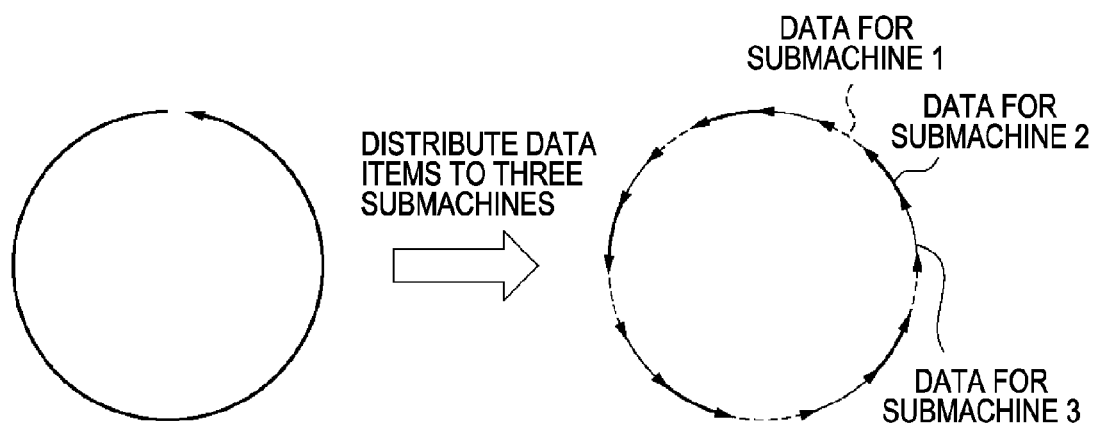
FIG. 11 shows an example method of dividing projection-image-data items at discrete angles.

(3) The data items are distributed to the submachine for each predetermined view angle, as shown in FIG. 11. For example, the data items are distributed to each submachine every predetermined view angle so that the total of the view angles assigned to each submachine becomes a 120-degree angle and the total of the data items distributed to each submachine becomes 340 views.

Figure 12:
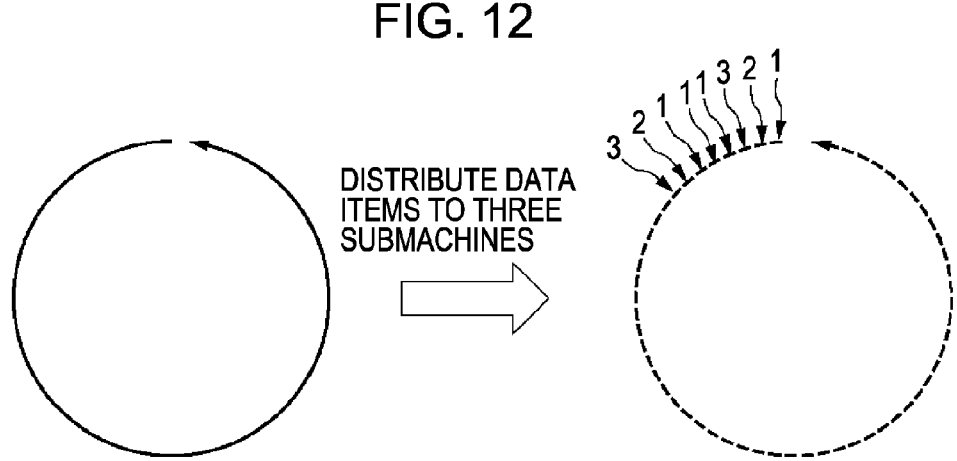
FIG. 12 shows an example method of distributing projection-image-data items at fine sampling angles.

(4) The data items are sequentially transmitted to the submachines in order of the time when the processing is finished. For example, if the submachine 1 is a high-speed machine and the submachines 2 and 3 are low-speed machines, the number of data items assigned to the submachine 1 is increased as shown in FIG. 12, because the data items are sequentially assigned to the submachines in order of the time when the processing is finished. According to this method, the projection-image-data latency of each submachine is decreased. Although the data items are assigned in order from 0 degree in FIG. 12, the data items may be assigned at discrete angles.

In the present embodiment, the host machine distributes the projection-image-data items to at least one submachine in projection angles. Therefore, the distribution processing can be performed not only for the back-projection-calculation processing, but also for the pre-processing, the convolution-calculation processing, and the post-processing. Therefore, the reconstruction processing can be performed with increased speed by performing the pre-processing, the convolution-calculation processing, the back-projection-calculation processing, and the post-processing through the distribution processing.

Second Embodiment

As described above, since X-ray-CT apparatuses that have been available in recent years can capture many fine slice images at the same time, the X-ray-CT apparatuses have to reconstruct these slice images with high speed, which places the X-ray-CT apparatuses under heavy load. Further, it is burdensome for a doctor to have to view these slice images. According to a second embodiment of the present invention, the function of selecting slice images that should be viewed from the many slice images is added.

Figure 14:
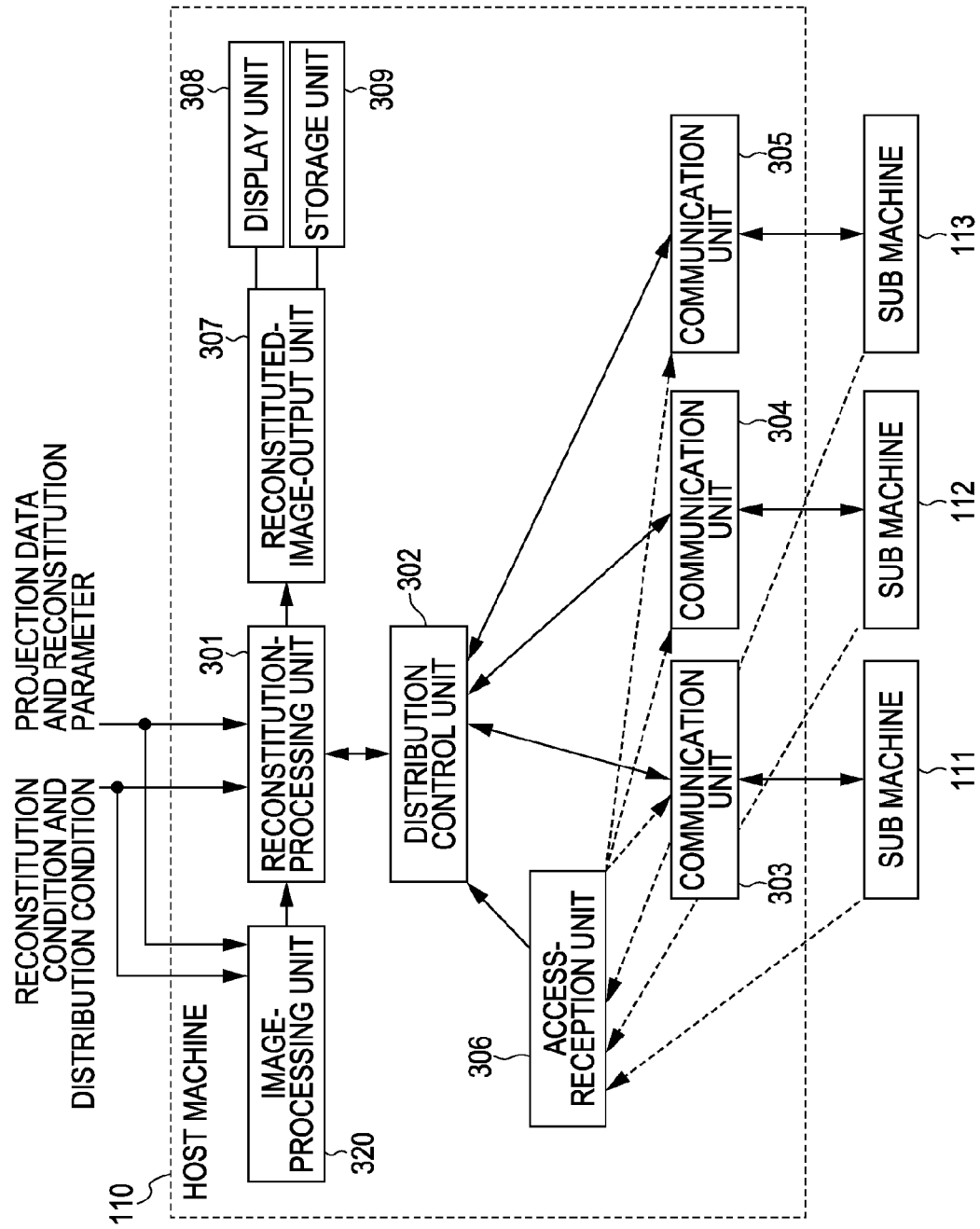
FIG. 14 is a functional block diagram of a host machine according to a second embodiment of the present invention.
Figure 15:
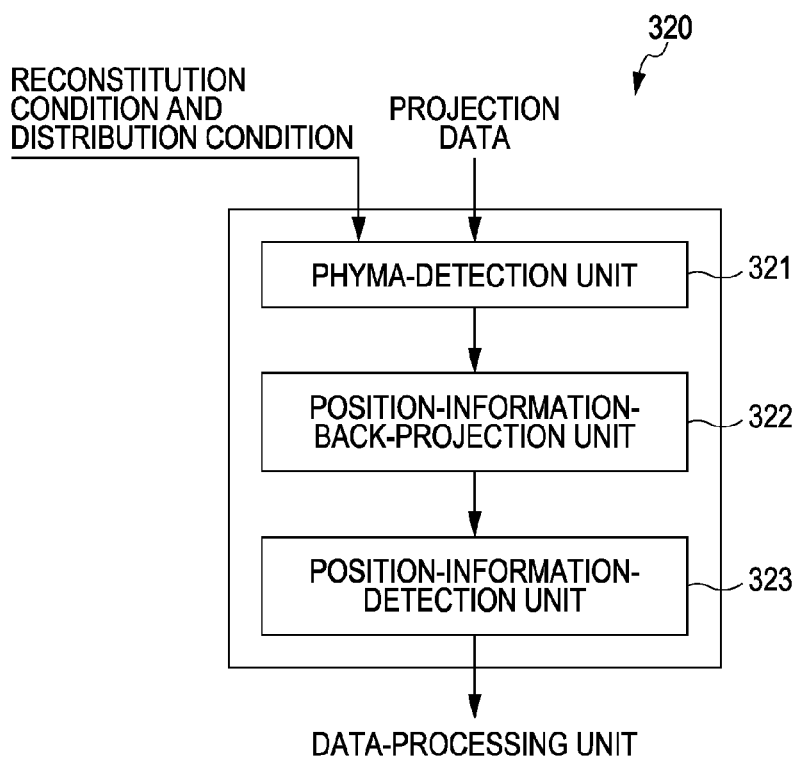
FIG. 15 shows the specific configuration of an image-processing unit according to the second embodiment.

FIG. 14 is the functional block diagram of the host machine 110 according to the second embodiment. The configuration shown in FIG. 14 is similar the configuration in FIG. 3, with the addition of an image-processing unit 320. FIG. 15 shows the detailed configuration of the image-processing unit 320.

Figure 16:
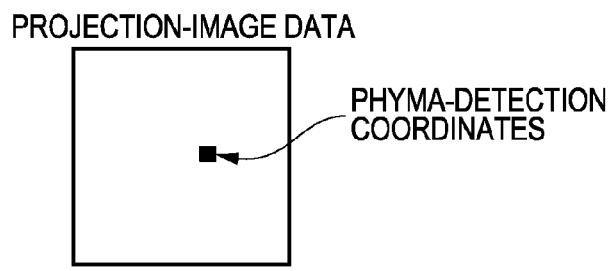
FIG. 16 illustrates processing of a phyma-detection unit according to the second embodiment.
Figure 17:
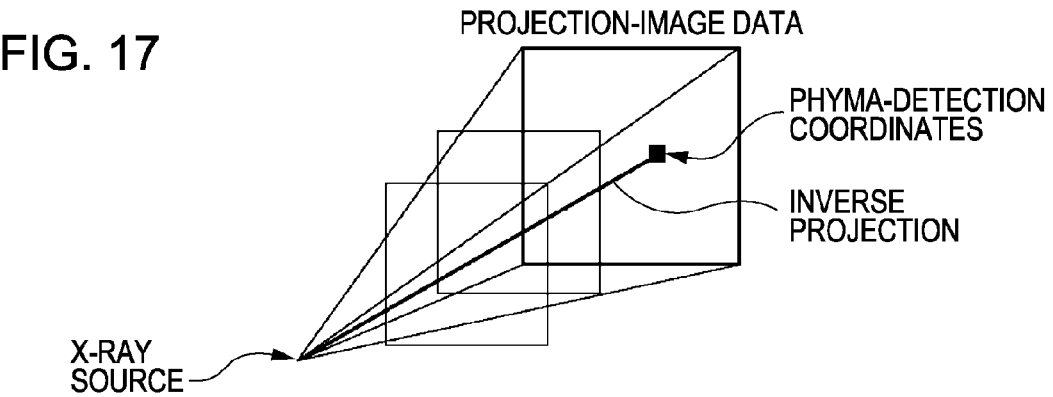
FIG. 17 illustrates processing of a position-information-back-projection unit according to the second embodiment.
Figure 18:
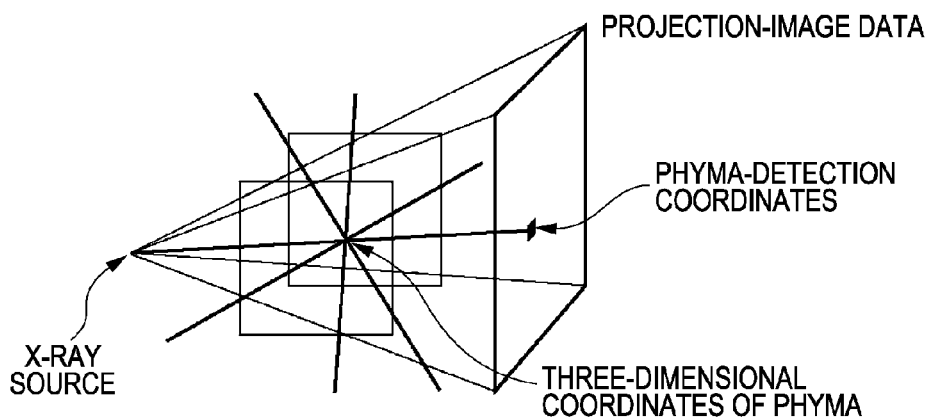
FIG. 18 illustrates processing of a position-information-detection unit according to the second embodiment.

A phyma-detection unit 321 performs image processing for the projection image of each captured view (projection-image data), and detects a phyma (see FIG. 16). Although the phyma detection can be achieved in various ways, a portion having a low pixel value and at least predetermined area is determined to be the phyma. A position-information-back-projection unit 322 back-projects the coordinates of the phyma detected from the projection image of each captured view (see FIG. 17). A position-information-detection unit 323 detects information about the position of the phyma in the three-dimensional coordinates, based on the result of the back projection performed by the position-information-back-projection unit 322 (see FIG. 18).

Here, the position-information-inverse-projection unit 322 may perform the back-projection not only for the coordinates where the phyma is detected. Namely, the position-information-back-projection unit 322 may perform the back projection by giving a weight inversely proportional to the distance from the detected coordinates. Further, the position-information-detection unit 323 sets the threshold value of the weight and determines a section having a weight of which value is at least equivalent to the threshold value to be the three-dimensional coordinates where the phyma exists.

Next, an example where processing of the above-described image-processing unit 320 is performed through the distribution processing performed by using the submachines will be described.

When the processing of the image-processing unit 320 is performed through the distribution processing, any one of (1) "phyma detection only", (2) "position-information-back projection only", or (3) "phyma detection and position-information-back projection" can be distributed to the submachine based on the distribution condition.

Figure 19:
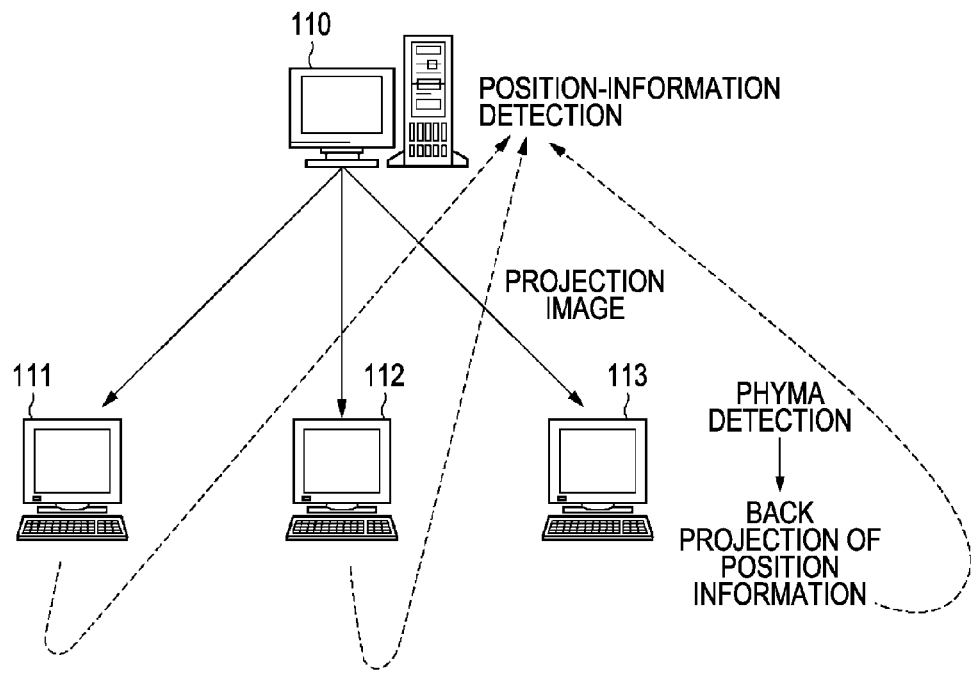
FIG. 19 illustrates example distribution processing performed for phyma detection and back projection of position information according to the second embodiment.

Of the above-described processing procedures, an example of the processing procedures corresponding to (3) "phyma detection and position-information-back projection" will described. As shown in FIG. 19, each of the submachines 111, 112, and 113 performs the phyma detection for a projection image transmitted thereto and back-projects the position information. The submachines 111, 112, and 113 transmit data on the result of the back projection to the host machine 110, and the host machine 110 detects the position information based on the entire back-projection information.

At that time, two methods may be considered to distribute projection-image-data items to the submachines. According to the first method, the projection-image-data items are distributed in units of one projection angle (a single view), as shown in FIG. 20. According to the second method, the projection-image-data items corresponding to at least two views are collectively distributed, where each of the projection-image-data items is divided along the direction intersecting the body axis of the subject, as shown in FIG. 21.

According to the method for distributing the projection-image-data items in the unit of a single view, as shown in FIG. 20, no border occurs in the distributed image so that the phyma detection can be achieved without any trouble. On the other hand, if each of the images corresponding to the projection-image-data items is divided along the direction intersecting the body axis of the subject and the projection-image-data items are distributed, as shown in FIG. 21, the border is generated along a break in the projection-image-data item, which makes it difficult to detect a phyma existing in the break.

Figure 22:
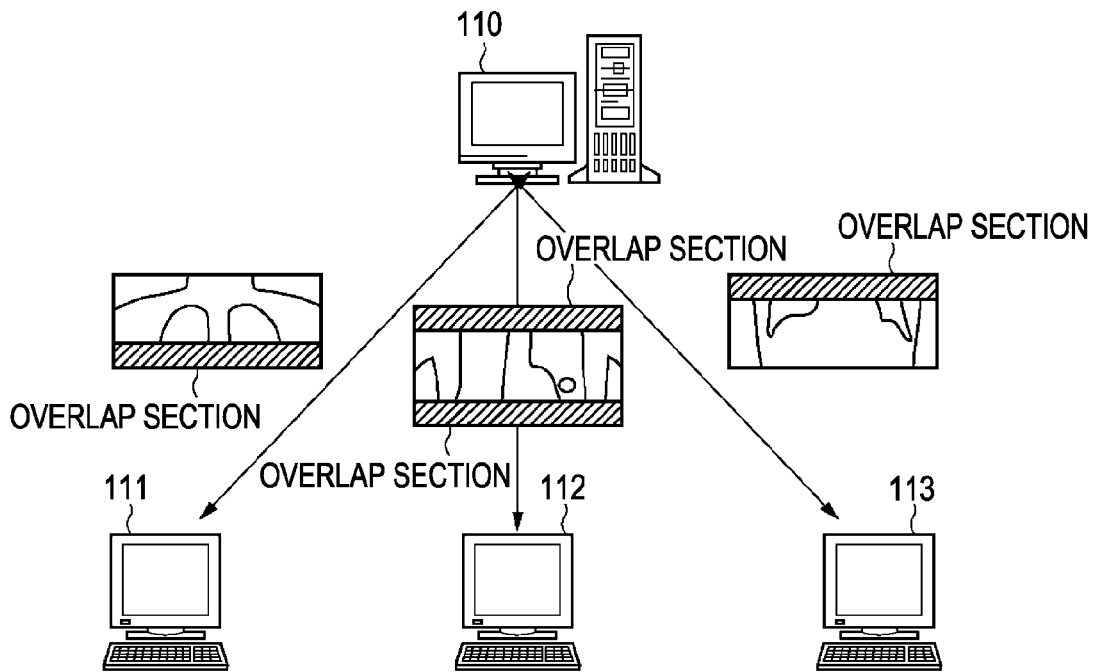
FIG. 22 illustrates the method of providing overlap sections in divided images.
Figure 23:
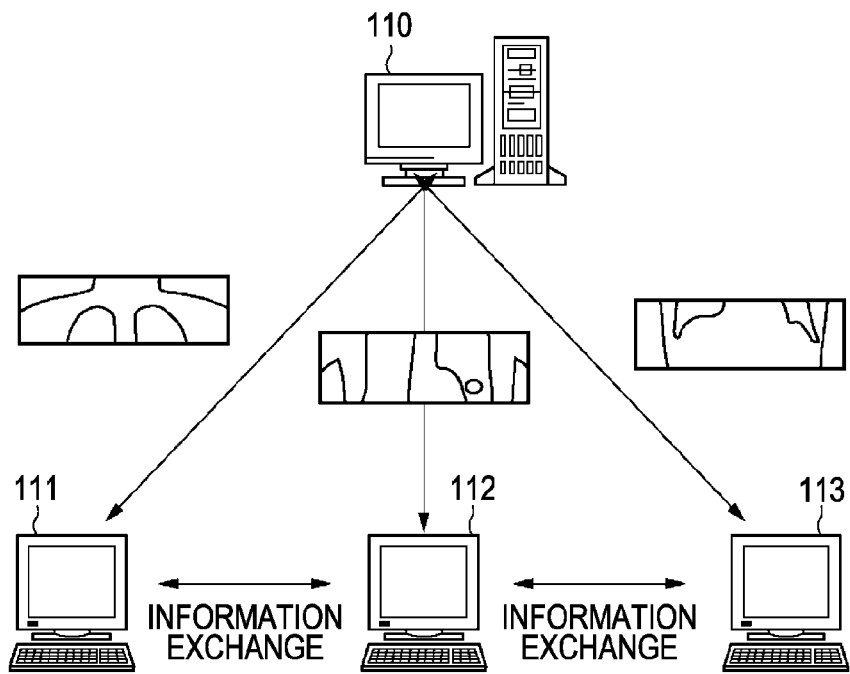
FIG. 23 illustrates the method of exchanging information items between submachines.

For solving the above-described problem, the method of providing each of divided images with an overlap section large enough to cover a target phyma and distributing data items (see FIG. 22), the method of detecting the target phyma by exchanging items of the phyma information obtained near the border between the submachines (see FIG. 23), etc. may be provided.

According to the present embodiment, the phyma image is detected from the projection image of each view and the phyma image is back-projected on the three-dimensional coordinates so that the coordinates of the phyma can be detected before the reconstruction-processing unit 301 performs the reconstruction processing. Consequently, the target of the reconstruction processing performed by the reconstruction-processing unit 301 can be limited to a slice image obtained at the position where the phyma image is detected, for example.

Further, in the present embodiment, the host machine 110 and the submachines 111 to 113 are connected to one another via the network. However, the host machine 110 and the submachines 111 to 113 may be provided in a single apparatus, as processing devices connected to a bus.

Third Embodiment

Figure 24:
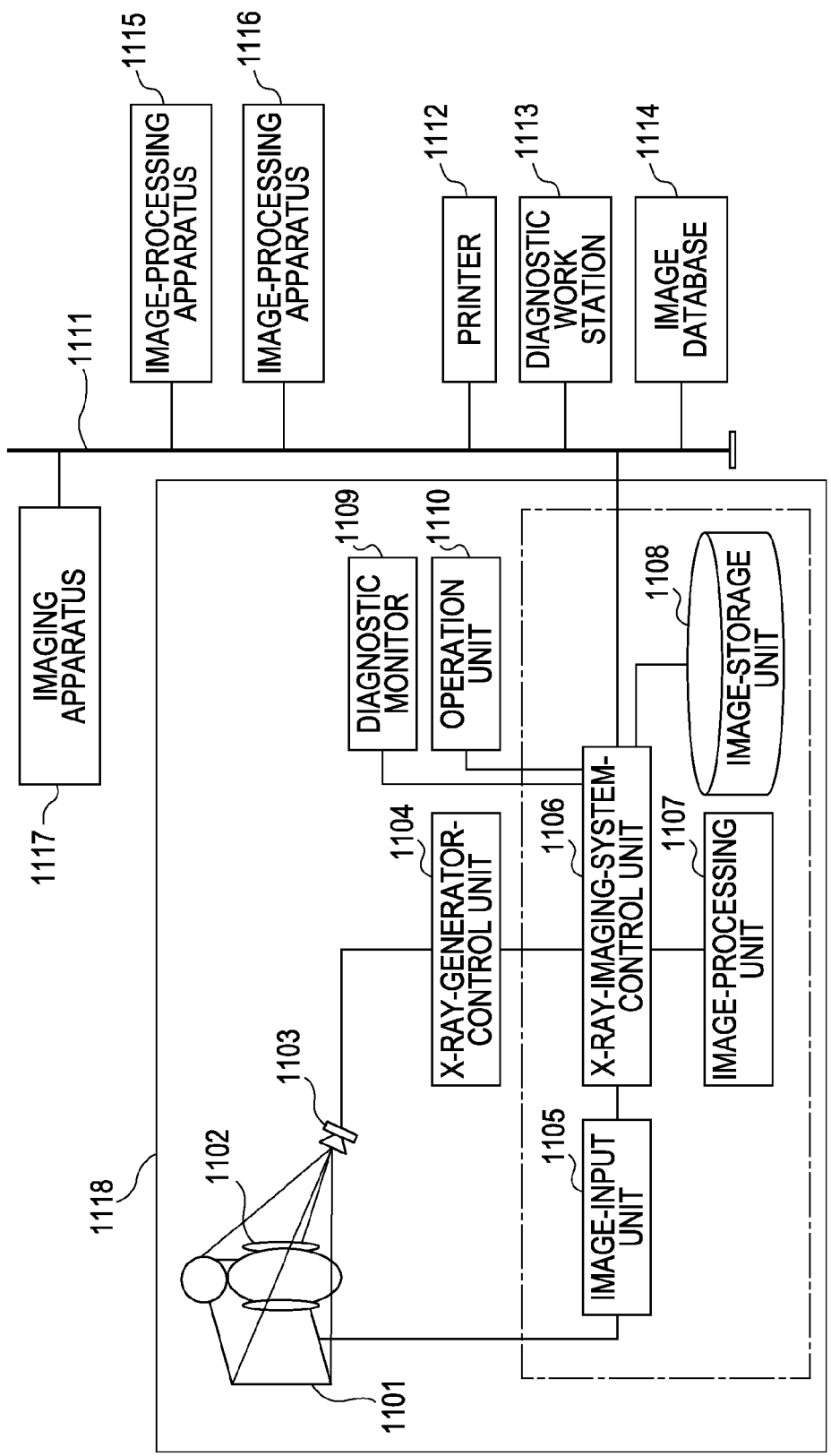
FIG. 24 schematically shows the configuration of a cone-beam-X-ray-CT apparatus.

Hereinafter, a third embodiment of the present invention will be described. FIG. 24 shows a system of the third embodiment.

A printer 1112 is configured to print a medical image. An image-diagnostic-work station 1113 is provided to perform image diagnostics. An image database 1114 is configured to store data on captured images and referred to as picture-archiving-and-communication systems (PACS), etc. An imaging apparatus 1117 is typified by an X-ray-CT apparatus, a magnetic-resonance-imaging (MRI) apparatus, etc. and referred to, for example, as a modality. Data on an image captured by the imaging apparatus 1117 is displayed on a diagnostic monitor 1109, stored in an image-storage unit 1108, or transmitted to the printer 1112, the image-diagnostic-work station 1113 and/or the image database 1114, etc. via a network 1111. In a filmless environment, the printer 1112 is not needed.

Imaging apparatus 1118 is provided as an example of a modality. More specifically, imaging apparatus 1118 is a cone-beam-X-ray-CT apparatus.

An X-ray-imaging-system-control unit 1106 performs the entire imaging control, image collection, image processing, and image outputting. When the X-ray-imaging-system-control unit 1106 instructs an X-ray-generator-control unit 1104 to generate an X-ray, an X-ray source 1103 generates the X-ray under the control of the X-ray-generator-control unit 1104, and the X-ray is transmitted through a patient 1102 who is the object and detected by an X-ray detector 1101. Data on the detected X-ray is transmitted to an image-input unit 1105 as projection-image-data items. Then, while the X-ray source 1103 and the X-ray detector 1101 are rotated, where the patient 1102 who is the object is determined to be the rotation center, the projection-image-data items are collected for each predetermined rotation angle.

Here, a rotation table (not shown) or the like may be provided on the part where the patient 1102 is placed so that the patient 1102 can be rotated, and the patient 1102 may be rotated while maintaining the position relationship between the X-ray source 1103 and the X-ray detector 1101. The image-processing unit 1107 performs image processing for the transmitted projection-image-data items corresponding to each rotation angle so that a group of tomographic images is generated, where the image processing includes the pre-processing including the correction and the log conversion of the X-ray detector 1101, the reconstruction processing, etc. Further, an operation unit 1110 performs various operations including a window operation for a displayed image, a switch-display operation for a body-axis-directional-tomographic image, a section-change operation, a three-dimensional-surface-display operation, etc. Each of apparatuses 1115 and 1116 is an image-processing apparatus. Although the two image-processing apparatuses are provided in the present embodiment, at least one image-processing apparatus may be provided without being limited to the above-described configuration.

Figure 25:
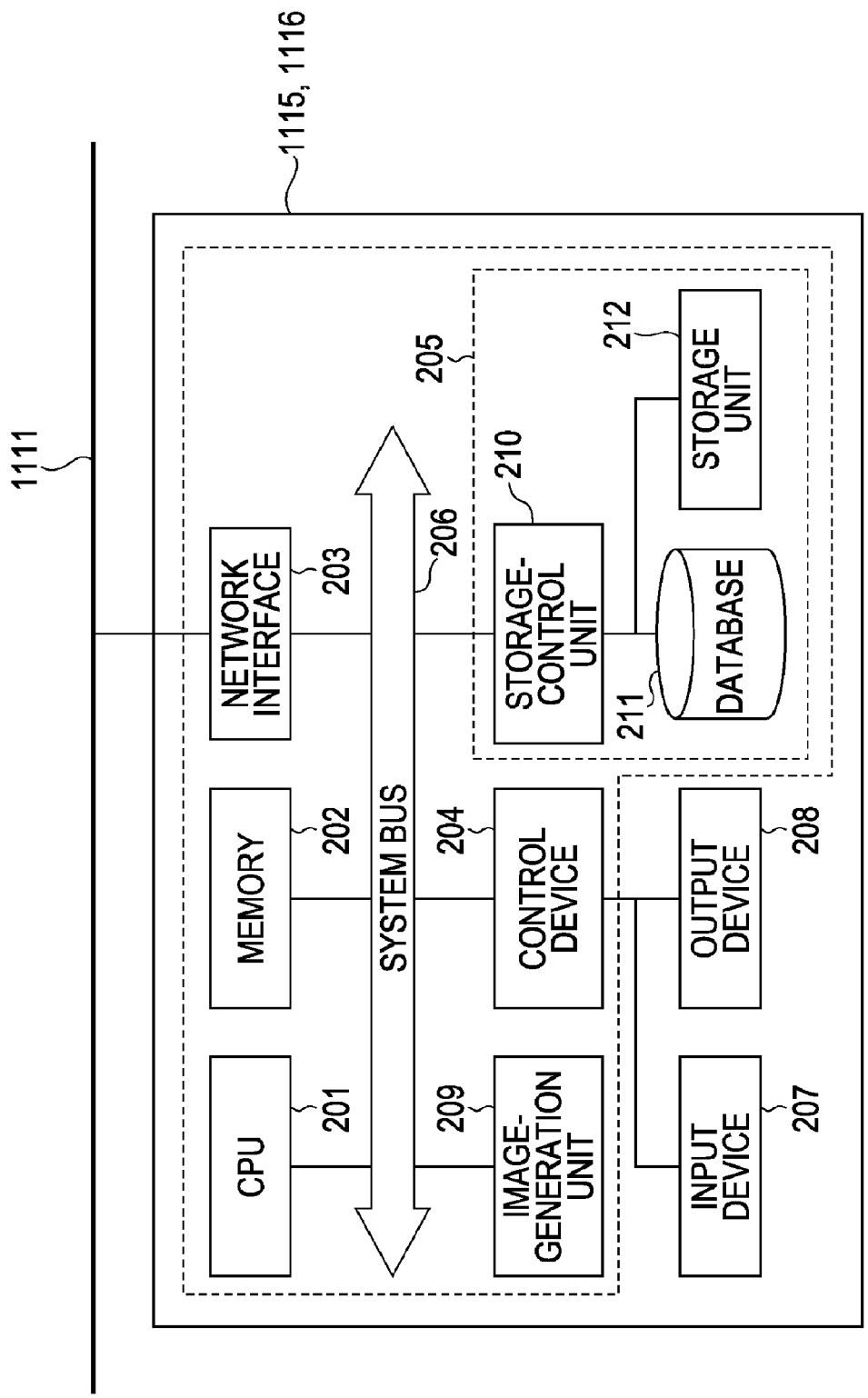
FIG. 25 is a block diagram of a computer system provided according to a third embodiment of the present invention.

Operations performed by the image-processing apparatuses 1115 and 1116 that are used in the present embodiment can be achieved as functions performed through the execution of a program of a computer system (hardware) shown in FIG. 25, for example. FIG. 25 shows a computer system achieving the imaging apparatus 1118 and/or the image-processing apparatuses 1115 and 1116. The computer system includes a CPU 201, a memory 202, a network I/F 203, a control device 204 controlling an input device 207 and an output device 208, a storage device 205 including a storage-control unit 210 controlling a database 211 storing patient information and a storage unit 212 storing image data, and an image-generation unit 209 that are connected to one another via a system bus 206. In addition, the computer system may include a large-scale-integrated (LSI) circuit and/or an application-specific-integrated circuit (ASIC).

Next, the processing flow of the present embodiment will be described with reference to the flowchart of FIG. 26.

First, CT imaging is performed in step S301. The CT imaging is performed through the imaging apparatus 1118.

Figure 29:
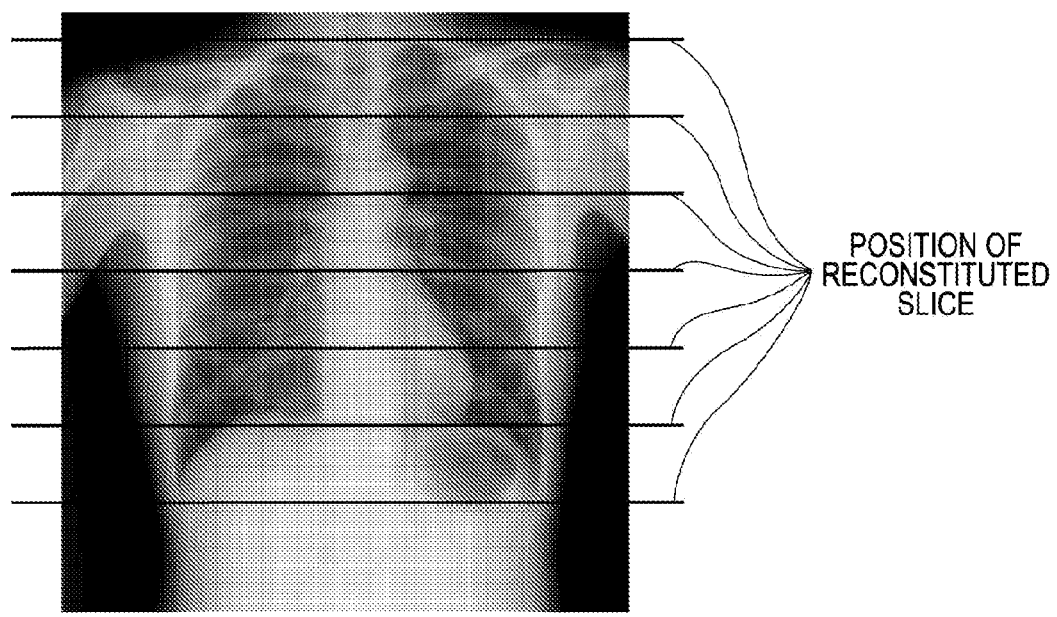
FIG. 29 is a conceptual diagram illustrating the specification of a slice plane for reconstruction.

Next, the X-ray-imaging-system-control unit 1106 detects the specification of a slice plane in step S302. The slice-plane specification is performed by operating the operation unit 1110 attached to the imaging apparatus 1118 while viewing the diagnostic monitor 1109. The slice-plane specification may be performed through either the method of selecting a slice plane by displaying a simple-radiographic image of the subject or the method of selecting the slice plane by displaying the projection image of the subject. For example, the slice plane of a tomographic image for reconstruction is specified, as shown in FIG. 29. As the gap between the top slice plane and the bottom slice plane decreases, the amount of three-dimensional-image information increases. Otherwise, as the gap between the top slice plane and the bottom slice plane increases, the three-dimensional-image-information amount decreases.

Next, in step S303, the X-ray-imaging-system-control unit 1106 confirms the number of processing nodes (the number of image-processing apparatuses performing processing). The processing-node number is determined based on the state of the image-processing apparatus 1115 and/or the image-processing apparatus 1116 connected to the imaging apparatus 1118 via the network 1111. It is confirmed whether each node, that is, the image-processing apparatus connected to the network, is in the state of readiness to perform the image processing. There are various methods for determining the state of readiness that are well-known in the art, and any of these methods are applicable, and thus a detailed description of any particular method is omitted herein. When the image-processing apparatus 1115 and/or the image-processing apparatus 1116 is not operable, the reconstruction processing may be performed by the imaging apparatus 1118. Next, in step S304, the X-ray-imaging-system-control unit 1106 determines the amount of data for distribution.

Figure 30:
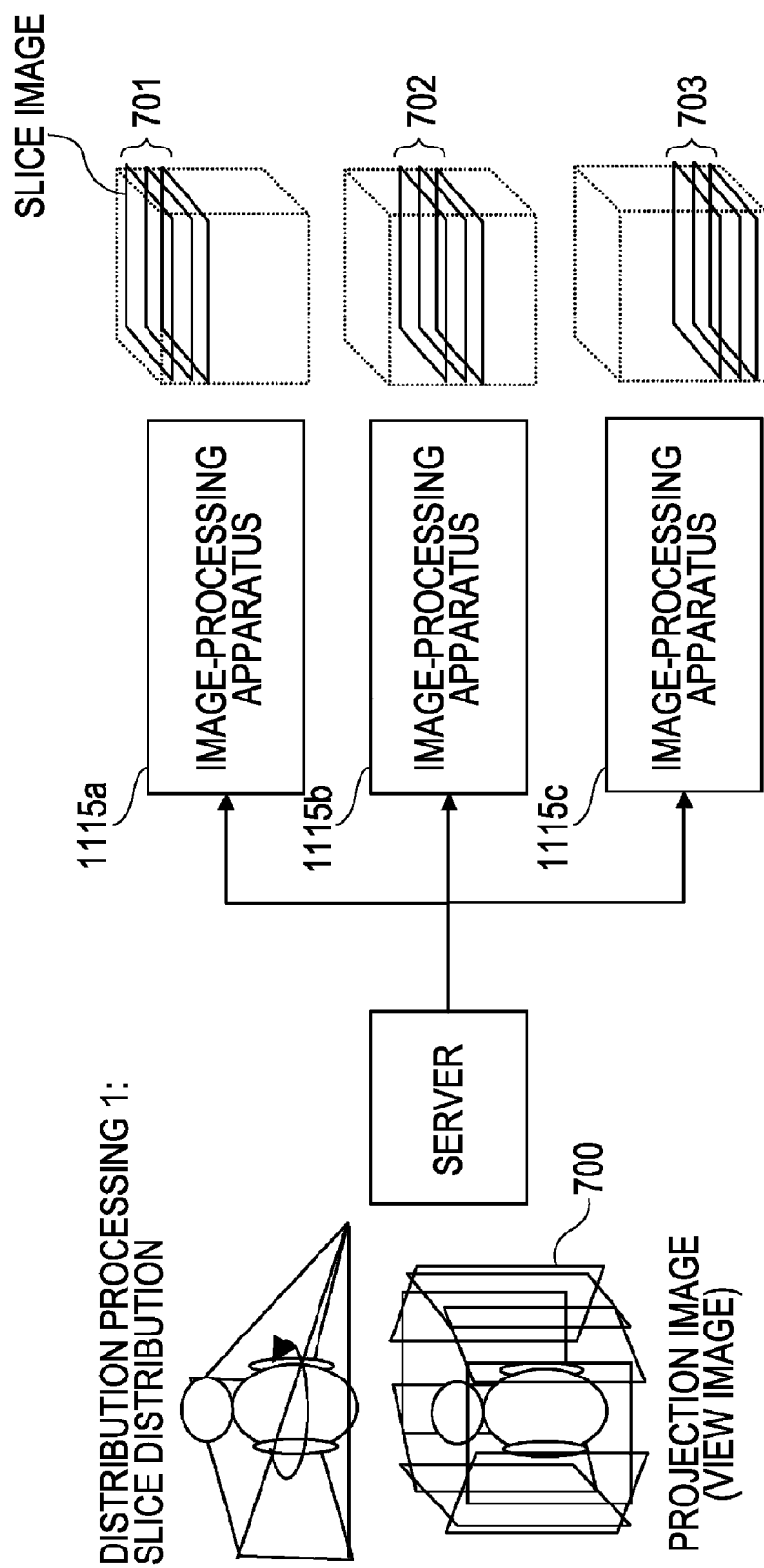
FIG. 30 shows example distribution of reconstruction.

An example of the reconstruction-processing distribution will now be described. When projection images 700 shown in FIG. 30 are acquired, the reconstruction processing is usually performed for all of the projection images 700 so that slice images are generated. According to the example shown in FIG. 30, three image-processing apparatuses 1115a, 1115b, and 1115c are provided. Image processing is distributed among the apparatuses so that processing for slice images generated in an area 701 is distributed to the image-processing apparatus 1115a, processing for slice images generated in an area 702 is distributed to the image-processing apparatus 1115b, and processing for slice images generated in an area 703 is distributed to the image-processing apparatus 1115c. Therefore, projection-image data required for the image-processing apparatus 1115a corresponds only to the upper part of the projection image, because the upper part is the area required to generate the slice image. Similarly, projection-image data required for the image-processing apparatus 1115b corresponds to the middle area of the projection image, and that required for the image-processing apparatus 1115c corresponds to the lower area of the projection image.

Next, in step S305, the X-ray-imaging-system-control unit 1106 distributes data which becomes the processing source among the image-processing apparatuses 1115, 1116. According to the data distribution, the projection data corresponding to an area necessary to perform the reconstruction processing, data on a necessary slice position, data on image-processing parameters, etc. are distributed among the image-processing apparatuses 1115, 1116.

Figure 31:
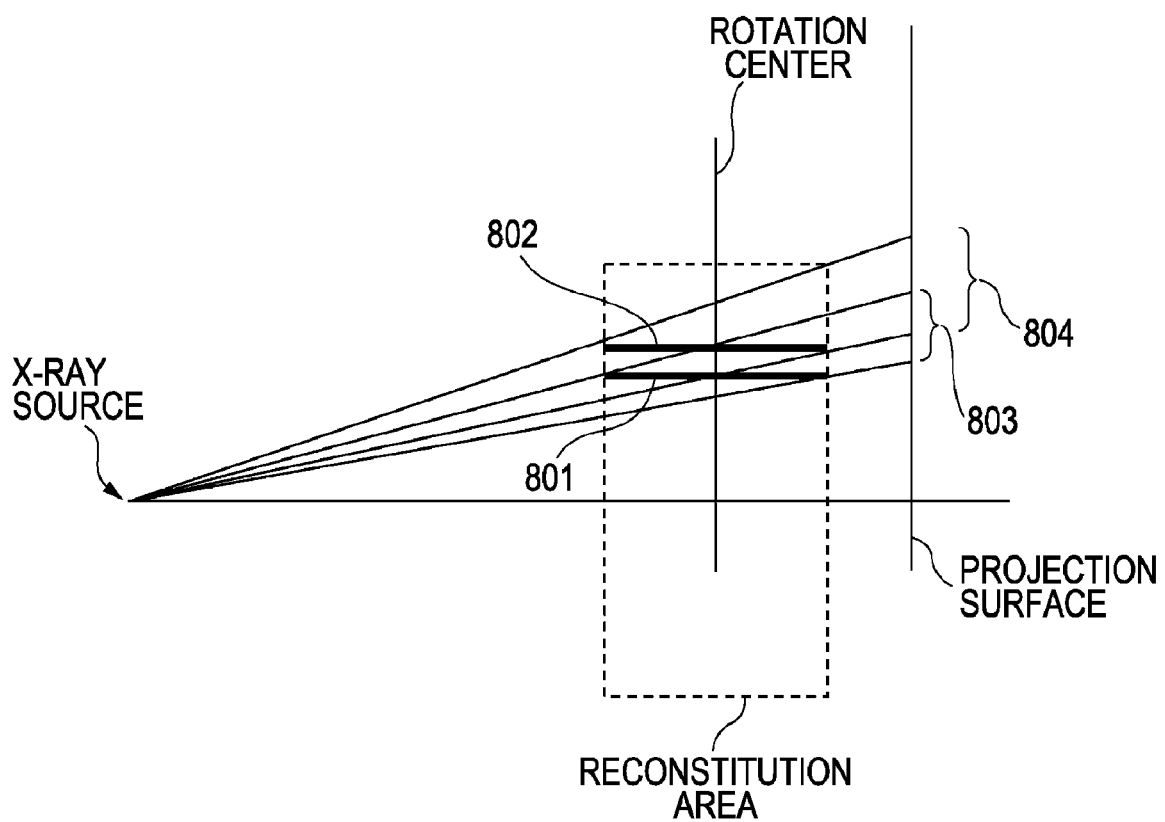
FIG. 31 shows a projection-data area necessary for the reconstruction.
Figure 32:
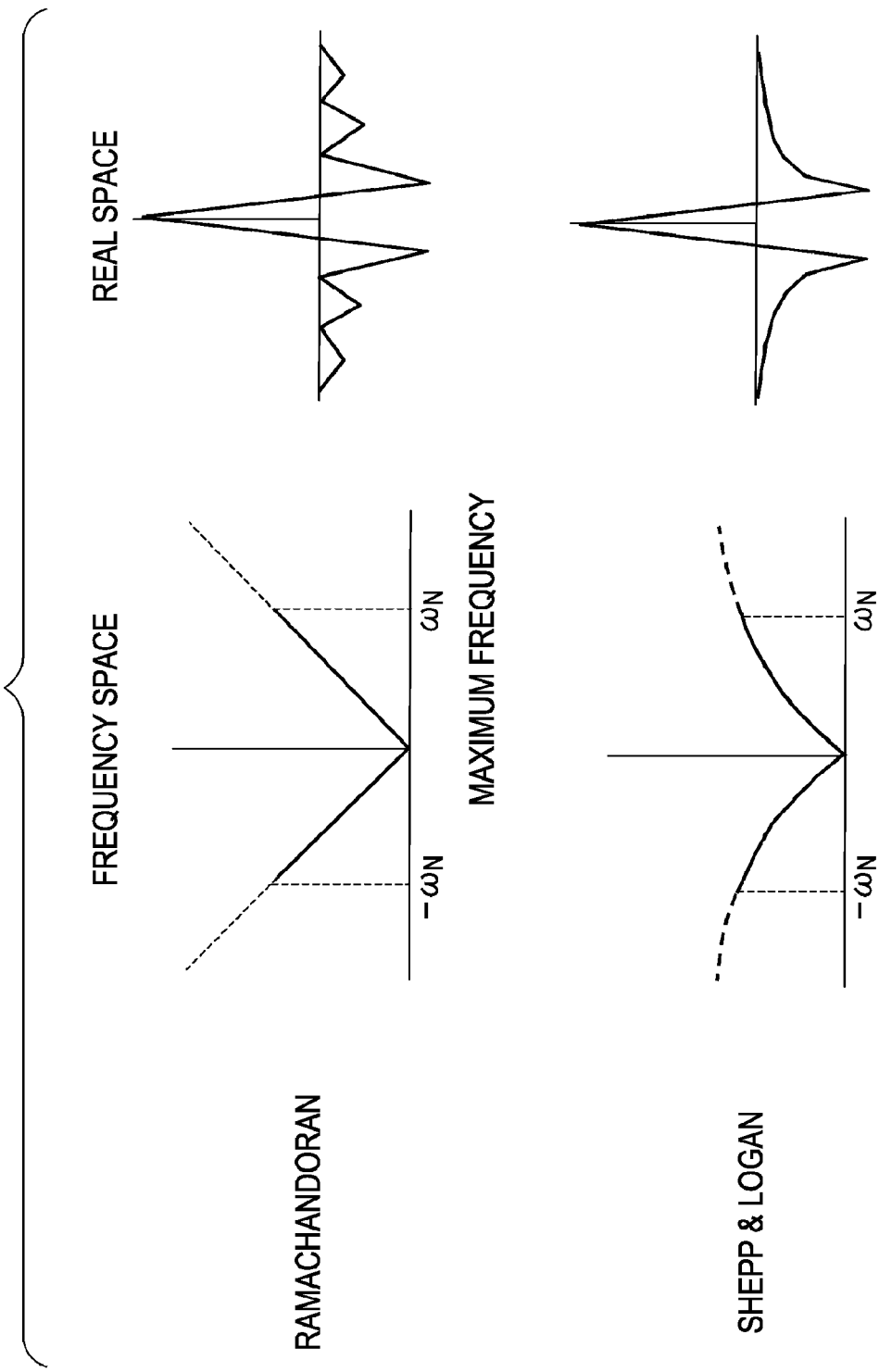
FIG. 32 is a conceptual diagram illustrating reconstruction functions.

Next, in step S306, the image-processing apparatus 1115 and/or the image-processing apparatus 1116 performs the reconstruction processing. Each image-processing apparatus performs the reconstruction processing immediately after transfer of the projection-image data is finished. Convolution processing is performed for a necessary area of a distributed processing area. For example, as shown in FIG. 31, a convolution area 803 is necessary to perform the reconstruction processing for a slice plane 801. Further, a convolution area 804 is necessary to perform the reconstruction processing for a slice plane 802. The projection-data areas of the convolution areas 803 and 804 overlap each other. Therefore, when the convolution processing is performed for each of the projection-data area 803 for the slice plane 801 and the projection-data area 804 for the slice plane 802, data on the processing result is reused by sharing data on the convolution result among slice processings, in order to avoid any unnecessary processing. The convolution processing is performed by obtaining the convolution of vertical-line data of the projection-image data and one-dimensional data referred to as a reconstruction function. FIG. 32 shows the function of Ramachandoran and Shepp & Logan, which are typical examples of the reconstruction function.

Figure 28:
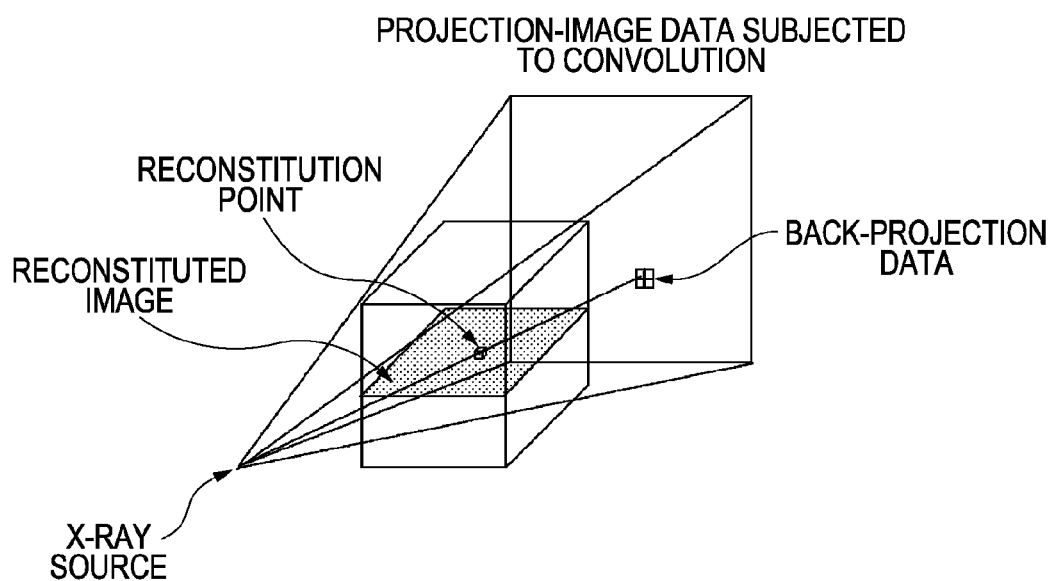
FIG. 28 is a conceptual diagram illustrating back-projection processing.

After that, back-projection processing is performed by using the projection-image data subjected to the convolution processing in the above-described manner. According to the back-projection processing, the coordinates of a point provided on a projection image that had passed through each pixel of a reconstructed image is obtained, and the pixel values of four points near the above-described coordinates are obtained through interpolation and added to one another, as shown in FIG. 28.

Figure 33:
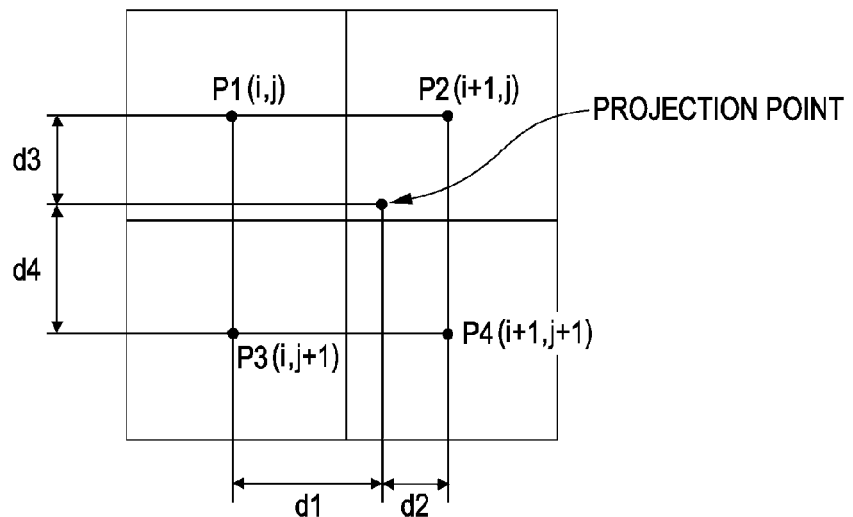
FIG. 33 is a conceptual diagram illustrating interpolation.

The geometrical relationship established during the interpolation is shown in FIG. 33. In FIG. 33, points P1, P2, P3, and P4 are the center points of the four pixels provided near the projection point. If the distances between the above-described four points and the projection point are determined to be d1, d2, d3, and d4, and the pixel values of the four pixels provided near the projection point are determined to be Q1, Q2, Q3, and Q4, the interpolation may be performed by using back-projection-data items V obtained through numerical expressions 1.

$$A1 = \frac{Q1 \times d2 + Q2 \times d1}{d1 + d2}$$

$$A2 = \frac{Q3 \times d2 + Q4 \times d1}{d1 + d2}$$

$$V = \frac{A1 \times d4 + Q2 \times d3}{d3 + d4}$$

[Numerical Expressions 1]

Then, the addition of the back-projection-data items V used for the above-described interpolation is performed for the entire projection-image data and all of the pixels, so that the reconstruction processing is completed. Thus, the tomographic image of a specified slice plane can be generated.

Figure 26:
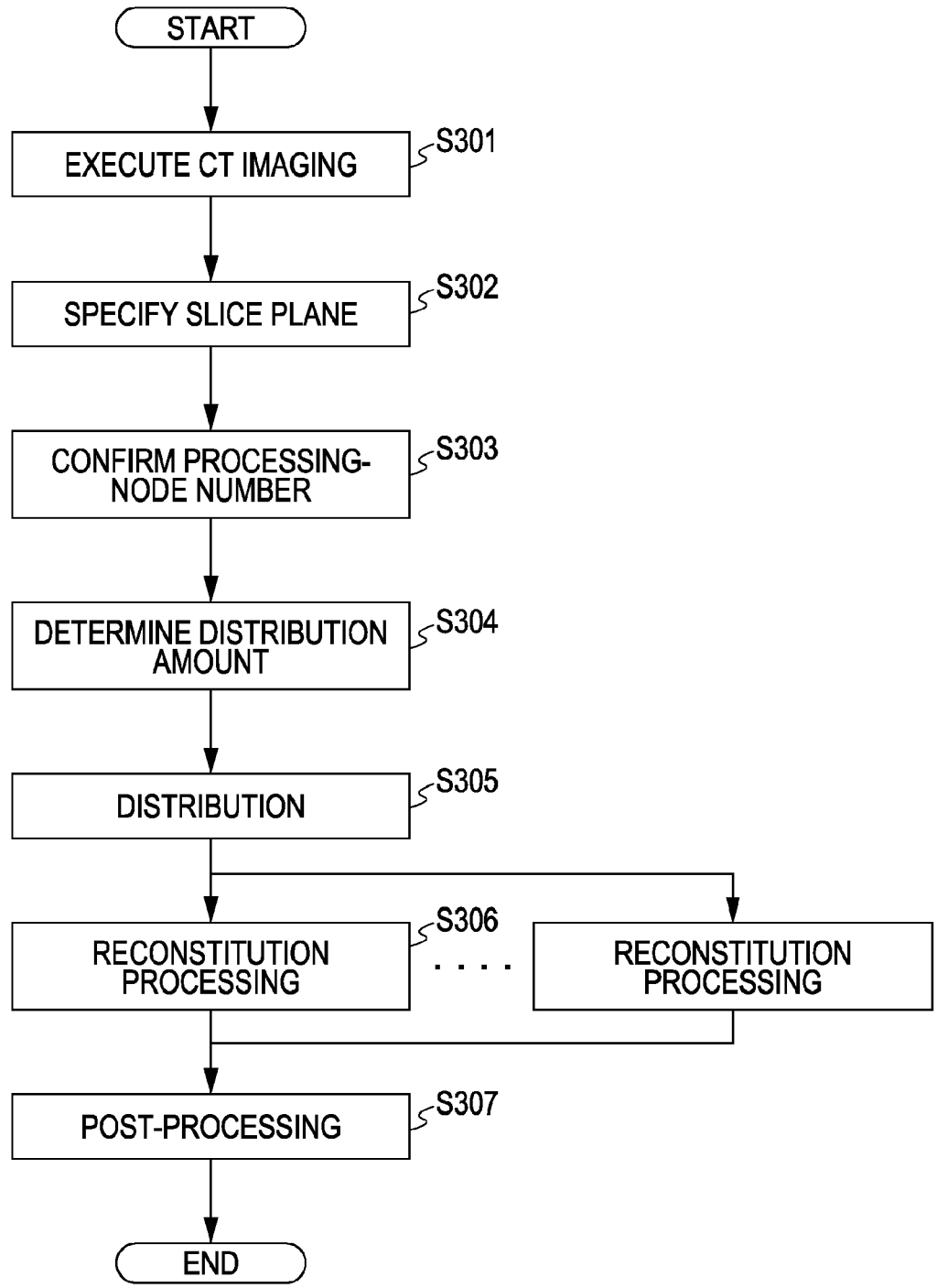
FIG. 26 is a flowchart showing processing procedures according to the third embodiment.
Figure 27:
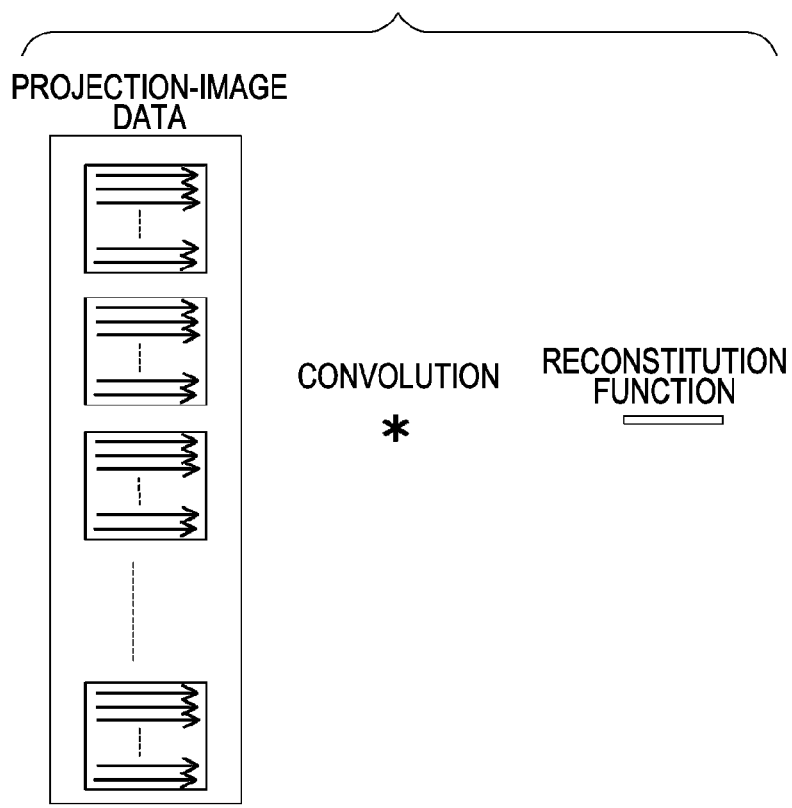
FIG. 27 is a conceptual diagram illustrating convolution processing.

Turning back to the flow of FIG. 26, post processing is performed in step S307. The post-processing is executed by returning processed slice-image data from each node, that is, the image-processing apparatus 1115 and/or the image-processing apparatus 1116 that had performed the reconstruction processing to the imaging apparatus 1118 via the network, and compiling the slice-image data through an integration unit 1403 of the X-ray-imaging-system-control unit 1106, as a three-dimensional reconstructed image. For compiling the slice-image data, the format of the slice-image data is converted into a medical-image-data format, unnecessary data stored in a memory and/or a hard disk is deleted, for example.

Next, the method of determining the distribution amount will be described in detail.

Figure 34:
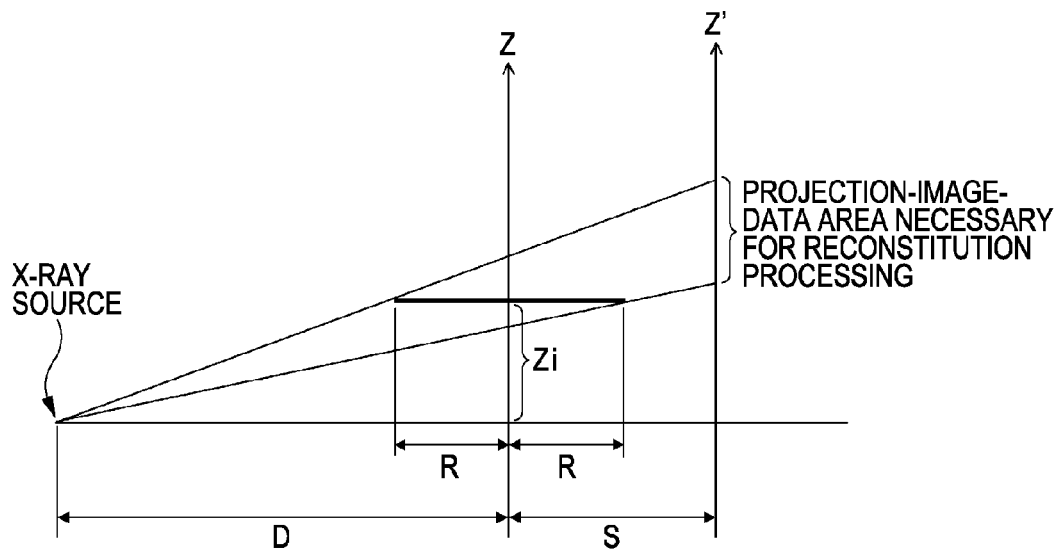
FIG. 34 illustrates the position of a specified reconstructed-slice plane on a reconstructed image.
Figure 35:
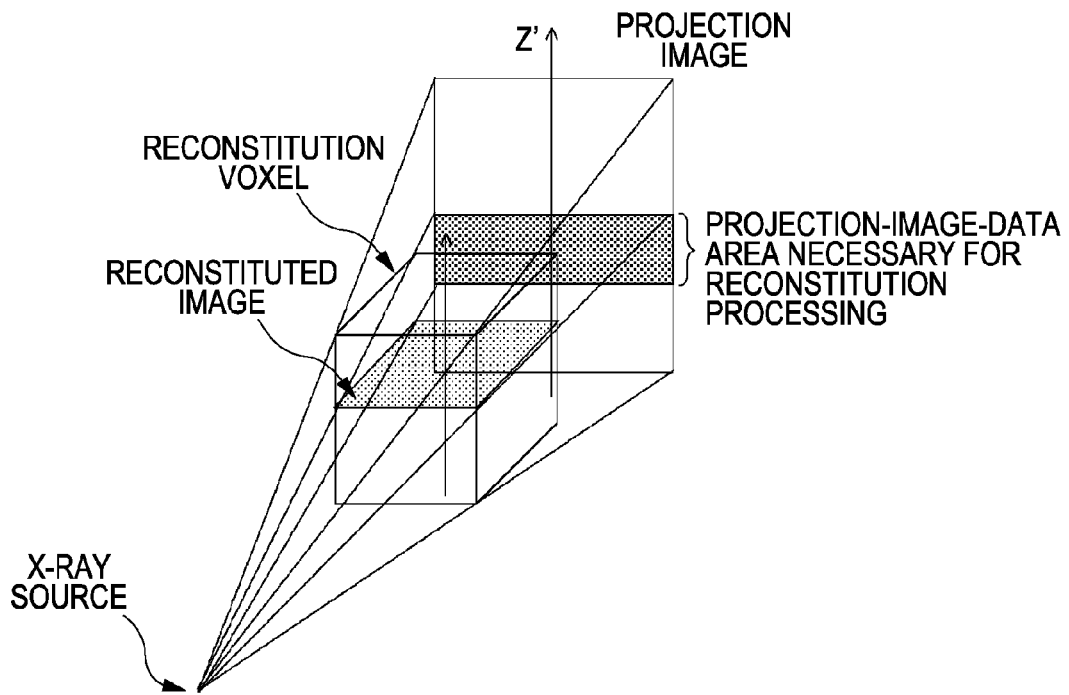
FIG. 35 illustrates the line area of a projection image necessary to perform the back-projection processing.

First, the reconstruction processing is performed by subjecting the projection-image data to the convolution processing, and back-projecting the projection-image data subjected to the convolution processing to each pixel of a reconstructed image. Next, processing required to reconstruct a single predetermined slice image will be described. Projection data required to reconstruct a predetermined slice plane is limited to a certain area of the projection image, as shown in FIG. 35. FIG. 34 shows the above-described position relationship. In FIG. 34, the processing area of a Z'-value on the projection image of a slice where a Z-value of the reconstructed image is Zi is shown by Numerical Expression 2, as below.

$$Zi \times (D+S)/(D+R) \sim Zi \times (D+S)/(D-R)$$ [Numerical Expression 2]

In Numerical Expression 2, the sign R indicates the radius of an reconstruction area (half of the vertical length and/or the lateral length of the reconstructed image), the sign D indicates the distance between the X-ray source and the rotation center (the center of the reconstructed image), and the sign S indicates the distance between the rotation center and a sensor. A predetermined point defined on a projection image Z' is shown by Numerical Expression 3 by using the sign Zi.

$$Z' = Zi \times (D+S)/D$$ [Numerical Expression 3]

Figure 36:
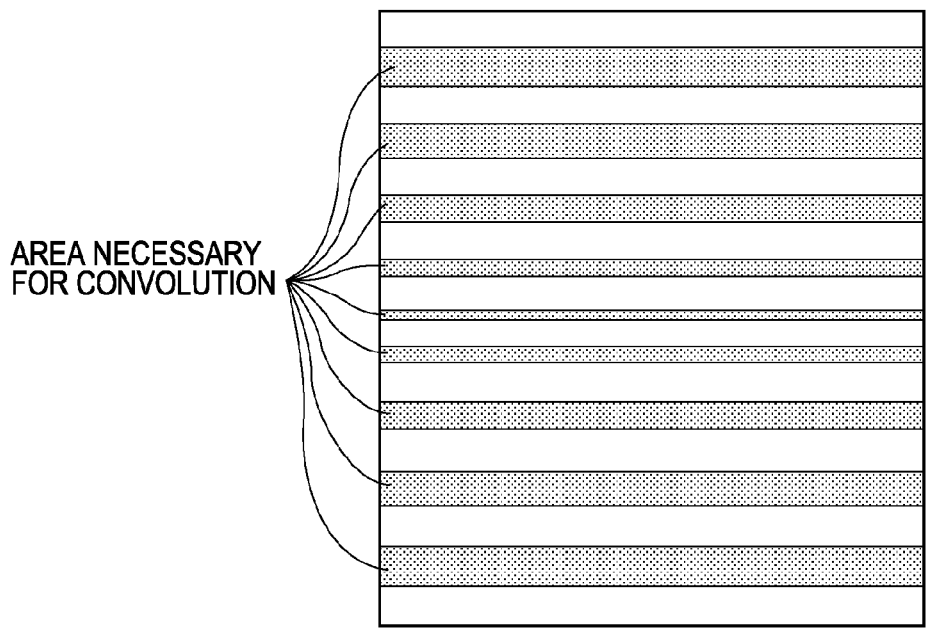
FIG. 36 is a conceptual diagram illustrating an area necessary to perform the back-projection processing.

Therefore, if the gap between slice planes for reconstruction may not be narrow, the entire projection-image data is not necessary for the reconstruction processing. Namely, the reconstruction processing can be performed based only on intermittent areas, as shown in FIG. 36. Further, the convolution processing may be performed only for the intermittent areas.

On the other hand, if the gap between the slice planes for reconstruction is narrow, for example, adjacent slice planes overlap each other, as shown in FIG. 31. Therefore, according to the configuration shown in FIG. 31, the convolution processing should be performed for the area extending from the lower part of the convolution area 803 to the upper part of the convolution area 804 only once.

Next, the method of distributing the reconstruction processing will be considered. As described above, as the Z-value |Zi| of the reconstructed image increases, namely, as the distance from the upper end and the lower end of the reconstruction area decreases, the amount of projection data necessary to generate a single slice image increases, which means that the processing time increases as the Z-value |Zi| increases. Therefore, a distribution method which allows for equalizing processing times as much as possible is derived. First, the time required to perform the reconstruction processing through a single image-processing apparatus is shown by Numerical Expression 4.

Processing time=$\{Zi(D+S)/(D-R)-Zi(D+S)/(D+R)\}*Con*Bp*Vn$ [Numerical Expression 4]

According to Numerical Expression 4, the sign Con indicates a time per a unit time relating to the convolution processing, the sign Bp indicates a time per a unit time relating to the back-projection processing, and the sign Vn indicates the number of projection images.

Here, when $(D+S)/(D-R)$ is determined to be a, $(D+S)/(D+R)$ is determined to be b, and $Con*Bp*Vn$ is determined to be c, and $C*(a+b)$ is determined to be d, Numerical Expression 4 can be rewritten into Numerical Expression 5.

Processing time=$dZi$ [Numerical Expression 5]

Next, the division number is determined to be M, the expression M/2=2 holds, k is determined to be a natural number, where the expression $0<k \leq m$ holds, and the maximum value of Zi is determined to be Ze. In that case, when Z(0) to Z(m) is divided by m, the distribution amount that should be processed through each of Z(0)~Z(1), Z(1)~Z(2), ..., Z(k−1)~Z(k), ..., Z(m−1)~Z(m) is one-mth of the entire processing amount. Therefore, the kth distribution amount Z(k−1)~Z(k) can be shown by Numerical Expressions 6.

$Z(k)=\sqrt{\{Z(k+1) \times Z(k+1) - Ze \times Ze/m\}}$, and
$Z(m)=Ze$ [Numerical Expressions 6]

More specifically, when the expressions Ze=10 and m=5 hold, and a reconstructed image is generated where the value of each of the gaps between the slice planes 0 to 10 is determined to be 1, the following expressions:

$Z(5)=Ze=10$, $Z(4)=\sqrt{\{Z(5)*Z(5)-Ze*Ze/m\}}=\sqrt{(80)}=8.9...$, $Z(3)=\sqrt{(60)}=7.7...$, $Z(2)=\sqrt{(40)}=6.3...$, $Z(1)=\sqrt{(20)}=4.4\ldots$, and $Z(0)=0$ hold. Although the method of handling decimal places varies based on settings and/or the courses of action of a facility, round-up processing is performed in the above-described embodiment. Thus, as for slice planes subjected to the reconstruction processing by each node, the slice planes 0 to 5 are reconstructed through m1, the slice planes 6 and 7 are reconstructed through m2, the slice plane 8 is reconstructed through m3, the slice plane 9 is reconstructed through m4, and the slice 10 is reconstructed through m5. Once slice planes for distribution are determined, a necessary data area can be obtained based on the value of Zi according to Numerical Expression 2.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-248180 filed on Sep. 25, 2007, which is hereby incorporated by reference herein in its entirety.

What is claimed is:

1. A computed-tomography system comprising:
a computed-tomography apparatus which performs scanning by radiating X-rays from at least two directions to a subject and collecting projection-image-data items;
a host machine, connected to the computed-tomography apparatus, configured to instruct the computed-tomography apparatus to perform the scanning and to perform reconstruction processing based on the projection-image-data items transferred from the computed-tomography apparatus; and
at least one submachine, connected to the host machine, configured to perform distribution processing for the reconstruction processing,
wherein the host machine includes:
an input unit configured to input a distribution condition defining a condition for the distribution processing;
a distribution unit configured to, based on the distribution condition, distribute projection-image-data items opposed to each other to the submachine as a set; and
a reception unit configured to receive data transmitted from the submachine, the data being subjected to the distribution processing, and
wherein the submachine includes:
an addition unit configured to perform addition, in a combination of the opposed projection-image-data items, for adding a pixel value of one of the projection-image data items to a pixel value of a coordinate position obtained by laterally reversing the other projection-image-data item, so as to be symmetric with respect to a rotation axis.

2. A computed-tomography system comprising:
a computed-tomography apparatus which performs scanning by radiating X-rays from at least two directions to a subject and collecting projection-image-data items;
a host machine, connected to the computed-tomography apparatus, configured to instruct the computed-tomography apparatus to perform the scanning and to perform reconstruction processing based on the projection-image-data items transferred from the computed-tomography apparatus; and
at least two submachines, connected to the host machine, configured to perform distribution processing for the reconstruction processing,
wherein the host machine includes:
a phyma-detection unit configured to detect a phyma from the projection-image-data item corresponding to each direction;
a position-information-back-projection unit configured to perform back projection for coordinates of the detected phyma; and
a position-information-detection unit configured to, based on a result of the back projection, detect position information in three-dimensional coordinates of the phyma,
wherein the submachine performs, based on a distribution condition, the distribution processing for at least one process performed in the phyma-detection unit and one process performed in the position-information-back-projection unit.

3. A computed-tomography system performing three-dimensional-reconstruction processing, the system comprising:
a radiation-imaging apparatus; and
at least two image-processing apparatuses,
wherein the radiation-imaging apparatus includes:
a determination unit configured to determine projection-image-data items of an area to be projection-image-data items to be distributed among the image-processing apparatuses, where the area is obtained through $Z(k)=\sqrt{\{Z(k+1)\times Z(k+1)-Ze\times Ze/m\}}$, and $Z(m)=Ze$, where a height difference between a center of an area which is a target of reconstruction and an X-line axis is determined to be $Z(i)$, a maximum value of the $Z(i)$ is determined to be Ze, a number of nodes for distribution is determined to be M, and M/2 is determined to be m, and k is determined to be a natural number,
where $0<k\leq m$ holds, so that
a distribution area distributed to a first node is an area shown as $Z(0)=0$ to $Z(1)$,
a distribution area distributed to a kth node is an area shown as $Z(k-1)$ to $Z(k)$, and
a distribution area distributed to an mth node is an area shown as $Z(m-1)$ to $Z(m)=Ze$; and
a distribution unit configured to distribute the determined projection-image-data items among the image-processing apparatuses,
wherein each of the image-processing apparatuses includes a processing unit configured to perform reconstruction processing for the distributed projection-image-data items.

* * * * *